US010004773B2

(12) United States Patent
Durst et al.

(10) Patent No.: US 10,004,773 B2
(45) Date of Patent: Jun. 26, 2018

(54) PLANT COMPOSITIONS AND METHODS AND USES THEREOF FOR TREATING ELEVATED GLUCOCORTICOID RELATED DISORDERS, AND ANXIETY

(71) Applicant: University of Ottawa, Ottawa (CA)

(72) Inventors: Tony Durst, Ottawa (CA); John Douglas Baker, Stirling (CA); John Thor Arnason, Ottawa (CA); Jose Miguel Wade, Celbridge (IE); Zulfiquar Merali, Ottawa (CA); Martha Mullally, Ottawa (CA); Christian Cayer, Cantley (CA); Stanley J. Alkemade, Arva (CA); Ana Francis Carballo, Ottawa (CA); Iqubal Velji, Montreal (CA)

(73) Assignee: University of Ottawa, Ottawa (CA)

(*) Notice: Subject to any disclaimer, the term of this patent is extended or adjusted under 35 U.S.C. 154(b) by 240 days.

(21) Appl. No.: 14/441,770

(22) PCT Filed: Nov. 8, 2013

(86) PCT No.: PCT/CA2013/000950
§ 371 (c)(1),
(2) Date: May 8, 2015

(87) PCT Pub. No.: WO2014/071507
PCT Pub. Date: May 15, 2014

(65) Prior Publication Data
US 2015/0283190 A1 Oct. 8, 2015

Related U.S. Application Data

(60) Provisional application No. 61/724,381, filed on Nov. 9, 2012.

(51) Int. Cl.
*A61K 36/185* (2006.01)
*A61K 45/06* (2006.01)
(52) U.S. Cl.
CPC ............ *A61K 36/185* (2013.01); *A61K 45/06* (2013.01)
(58) Field of Classification Search
None
See application file for complete search history.

(56) References Cited

U.S. PATENT DOCUMENTS 6,175,035 B1 * 1/2001 Draeger ............... C07J 63/008
424/769
6,228,850 B1 5/2001 Jaggi et al.
7,488,722 B2 2/2009 Durst et al.
2009/0068257 A1 3/2009 Leunis et al.

FOREIGN PATENT DOCUMENTS

CA 2474688 C 8/2003
WO 02/091858 A1 11/2002

OTHER PUBLICATIONS

Puniani, E.T., "Novel Natural Product Based Anti-Anxiety Therapy and Natural Insecticides", Ottawa-Carleton Chemistry Institute, University of Ottawa, Sep. 2003, 1-336 pages.
Mullally, M. "Anxiety-Reducing Tropical Plants: Phytochemical and Pharmacological Characterization of Souroubea sympetala and Piper amalago", Department of Biology, University of Ottawa, Nov. 10, 2011, pp. 1-192.
Mullally, M. et al., "Anxiolytic Activity of a Supercritical Carbon Dioxide Extract of Souroubea sympetala (*Marcgraviaceae*)", Phytother. Res. 25, Jul. 21, 2010, pp. 264-270.
Anagnostis, P. et al., "The Pathogenetic Role of Cortisol in the Metabolic Syndrome: A Hypothesis", Journal of Clinical Endocrinology and Metabolism, Aug. 2009, 94(8), pp. 2692-2701.
Baldwin, D. S. and Polkinghorn, C., "Evidence-based pharmacotherapy of generalized anxiety disorder", Int. J. Neuropsychopharmacol., 2005, vol. 8, pp. 293-302.
Barton B.A., "Salmonid Fishes Differ in Their Cortisol and Glucose Responses to Handling and Transport Stress", North American Journal of Aquaculture, 2000, vol. 62, pp. 12-18.
Bedard, T. et al, "Role of gastrin-releasing peptide and neuromedin B in anxiety and fear-related behavior", Behav. Brain Res., 2007, vol. 179, pp. 133-140.
Brown, E.S., et al., "Ketoconazole in bipolar patients with depressive symptoms: a case series and literature review", Bipolar Disorders, 2001, vol. 3, pp. 23-29.
Cain, C.K. et al, "Targeting memory processes with drugs to prevent or cure PTSD", Expert Opin. Investig. Drugs, 2012, 21(9), pp. 1323-1350.
Carroll, B.J. et al, "Pathophysiology of hypercortisolism in depression", Acta Psychiatr Scand, 2007, 115 (Suppl. 433): pp. 90-103.
Chandola, T. et al., "Chronic stress at work and the metabolic syndrome: prospective study", British Medical Journal, Feb. 14, 2006, pp. 1-5.
Cloos, J.M. and Ferreira, V., "Current use of benzodiazepines in anxiety disorders", Curr Opin Psychiatry, 2008, vol. 22, pp. 90-95.
Cohen, H. et al, "The Contribution of an Animal Model Toward Uncovering Biological Risk Factors for PTSD", Ann. N.Y. Acad. Sci. 2006, vol. 1071, pp. 335-350.
Cook, C.S. et al., "Prediction of in vivo drug interactions with eplerenone in man from in vitro metabolic inhibition data", Xenobiotica, Mar. 2004, vol. 34, No. 3, pp. 215-228.
Courtney, R. et al, "Modulation of 11β-Hydroxysteroid Dehydrogenase (11βHSD) Activity Biomarkers and Pharmacokinetics of PF-00915275, a Selective 11βHSD1 Inhibitor", J Clin Endocrinol Metab., Feb. 2008, 93(2), pp. 550-556.
Cruz, A.P.M. et al., "Ethopharmacological Analysis of Rat Behavior on the Elevated Plus-Maze", Pharmacology Biochemistry and Behavior, 1994, vol. 49, No. 1, pp. 171-176.

(Continued)

*Primary Examiner* — Susan Hoffman
(74) *Attorney, Agent, or Firm* — Bereskin & Parr LLP; Melanie Szweras

(57) ABSTRACT

The disclosure provides compositions containing preparations from plants of the family Marcgraviaceae and from plants of the family Platanaceae. The disclosure also provides methods and uses of plant preparations for treating anxiety, stress and glucocorticoid related disorders.

4 Claims, 10 Drawing Sheets

(56) References Cited

OTHER PUBLICATIONS

Dallman, M.F., "Stress-induced obesity and the emotional nervous system", Trends Endocrinol Metab., Mar. 2010, 21(3), pp. 159-165.
Davidson, J.R.T., "First-Line Pharmacotherapy Approaches for Generalized Anxiety Disorder", J Clin Psychiatry, 2009, vol. 70 (Suppl 2), pp. 25-31.
Davis, M. et al., "Fear-potentiated startle: a neural and pharmacological analysis", Behavioural Brain Research, 1993, vol. 58, pp. 175-198.
Davis, M. et al., "Pharmacological Treatments that Facilitate Extinction of Fear: Relevance to Psychotherapy", J. Am. Soc. Exp. Neurother, Jan. 2006, vol. 3, pp. 82-96.
Deporter, T.L. et al., "Harmonease Chewable Tablets reduces noise-induced fear and anxiety in a laboratory canine thunderstorm simulation: A blinded and placebo-controlled study", Journal of Veterinary Behavior, 2012, vol. 1, pp. 225-232.
Dinan, T., "Therapeutic options: Addressing the current dilemma", European Neuropsychopharmacology, 2006, vol. 16, Suppl 2, pp. S119-S127.
Durant, C. et al., "The Pharmacology of Anxiety", Current Topics in Behavioral Neurosciences 2, Sep. 2009, pp. 303-330.
Edwards, J.G., "Clinical Anxiety and its Treatment", Neuropeptides, 1991, vol. 19 (Suppl.), pp. 1-10.
File, S.E. et al., "Animal Tests of Anxiety", Current Protocols in Neuroscience, 2004, 8.3.1-8.3.22, Supplement 26, pp. 1-22.
Gamperl, A.K. et al., "Experimental control of stress hormone levels in fishes: techniques and applications", Reviews in Fish Biology and Fisheries, 1994, vol. 4, pp. 215-255.
Gathercole, L.L. and Stewart, P.M., "Targeting the pre-receptor metabolism of cortisol as a novel therapy in obesity and diabetes", Journal of Steroid Biochemistry and Molecular Biology, 2010, vol. 122, pp. 21-27.
Girardi, C.E.N. et al., "Contextual exploration previous to an aversive event predicts long-term emotional consequences of severe stress", Front. Behav. Neurosci., Oct. 2013, vol. 7, Article 134, pp. 1-8.
Gray, J.A. and McNaughton, N., "The Neuropsychology of Anxiety: An Enquiry into the Functions of the Septo-Hippocampal System, Second Edition", 2000, Oxford, UK: Oxford University Press, pp. 1-424.
Hajat, A. et al., "Socioeconomic and race/ethnic differences in daily salivary cortisol profiles: The Multi-Ethnic Study of Atherosclerosis", Psychoneuroendocrinology, 2010, vol. 35, pp. 932-943.
Herron M.E. et al., "Retrospective evaluation of the effects of diazepam in dogs with anxiety-related behavior problems", J Am Vet Med Assoc., Nov. 1, 2008, 233(9), pp. 1420-1424.
Hitchcock, J.M. and Davis, M., "Fear-Potentiated Startle Using an Auditory Conditioned Stimulus: Effect of Lesions of the Amygdala", Physiol. Behav., 1987, vol. 39, pp. 403-408.
Jahn, H. et al., "Metyrapone as Additive Treatment in Major Depression: A Double-blind and Placebo-Controlled Trial", Arch Gen Psychiatry, Dec. 2004, vol. 61, pp. 1235-1244.
Johansen, J.P. et al., "Molecular mechanisms of fear learning and memory", Cell, Oct. 28, 2011, 147(3), pp. 509-524.
Khan, S. et al., "Effects of acute restraint stress on endogenous adrenomedullin levels", NeuroReport, Sep. 9, 1999, vol. 10, No. 13, pp. 2829-2833.
Kim, T. et al., "Liver cirrhosis developed after ketoconazole-induced acute hepatic injury", Journal of Gastroenterology and Hepatology, 2003, vol. 18, pp. 1426-1429.
Kling, M.A. et al., "Glucocorticoid inhibition in the treatment of depression: Can we think outside the endocrine hypothalamus?", Depression and Anxiety, 2009, vol. 26, pp. 641-649.
Lawson, E.A. et al., "Hypercortisolemia Is Associated with Severity of Bone Loss and Depression in Hypothalamic Amenorrhea and Anorexia Nervosa", J Clin Endocrinol Metab., Dec. 2009, 94(12), pp. 4710-4716.
Leblond, V.S. et al., "Inhibition of Cortisol Secretion in Dispersed Head Kidney Cells of Rainbow Trout (*Oncorhynchus mykiss*) by Endosulfan, an Organochlorine Pesticide", General and Comparative Endocrinology, 2001, vol. 121, pp. 48-56.
Li, Y. et al., "Effect of Aging on Fatty Streak Formation in a Diet-Induced Mouse Model of Atherosclerosis", J Vasc Res., 2008, 45(3), pp. 205-210.
Maddox, S.A. et al., "A Naturally-Occurring Histone Acetyltransferase Inhibitor Derived from Garcinia indica Impairs Newly Acquired and Reactivated Fear Memories", PloS One, Jan. 2013, vol. 8, Issue 1, e54463, pp. 1-16.
Merali, Z. et al., "Nesfatin-1 increases anxiety- and fear-related behaviors in the rat", Psychopharmacology, 2008, vol. 201, pp. 115-123.
Milot, M.R. et al., "A refined blood collection method for quantifying corticosterone", Lab Anim., Mar. 2012, vol. 41, No. 3, pp. 77-83.
Mommsen, T.P. and Moon, T.W., "The Metabolic Potential of Hepatocytes and Kidney Tissue in the Little Skate, *Raja erinacea*", 1987, The Journal of Experimental Zoology, vol. 244, pp. 1-8.
Morgan, C.A. et al., "Fear-Potentiated Startle in Posttraumatic Stress Disorder", Biol. Psychiatry, 1995, vol. 38, pp. 378-385.
Mountney, C. et al., "Effects of gastrin-releasing peptide agonist and antagonist administered to the basolateral nucleus of the amygdala on conditioned fear in the rat", Psychopharmacology, 2008, vol. 200, pp. 51-58.
Mountney, C. et al., "The role of gastrin-releasing peptide on conditioned fear: differential cortical and amygdaloid responses in the rat", Psychopharmacology, Oct. 11,2006, vol. 189, pp. 287-296.
Parker, K.J. et al., "Neuroendocrine aspects of hypercortisolism in major depression", Hormones and Behavior, 2003, vol. 43, pp. 60-66.
Parsons, R.G. and Ressler, K.J., "Implications of memory modulation for post-traumatic stress and fear disorders", Nat. Neurosci., Feb. 2013, vol. 16, No. 2, pp. 146-153.
Passie, T. et al., "Mitigation of post-traumatic stress symptoms by Cannabis resin: A review of the clinical and neurobiological evidence", Drug Test. Anal., Jun. 26, 2012, vol. 4, pp. 649-659.
Pellow, S. et al., "Validation of open: closed arm entries in an elevated plus-maze as a measure of anxiety in the rat", Journal of Neuroscience Methods, 1985, vol. 14, pp. 149-167.
Ponomarev, I. et al., "Amygdala Transcriptome and Cellular Mechanisms Underlying Stress-Enhanced Fear Learning in a Rat Model of Posttraumatic Stress Disorder", Neuropsychopharmacol., 2010, vol. 35, pp. 1402-1411.
Rostagno, M.H., "Can Stress in Farm Animals Increase Food Safety Risk?", Foodborne Pathogens and Disease, 2009, vol. 6, No. 7, pp. 767-776.
Ruyet, J.P., et al. "Combined effects of water quality and stocking density on welfare and growth of rainbow trout (*Oncorhynchus mykiss*)", Aquat. Living Resour., 2008, vol. 21, pp. 185-195.
Sarris, J. et al., "Plant-Based Medicines for Anxiety Disorders, Part 2: A Review of Clinical Studies with Supporting Preclinical Evidence", CNS Drugs, 2013, vol. 27, pp. 301-319.
Schreck, C.B. et al., "Effects of stress on fish reproduction, gamete quality, and progeny", Aquaculture, 2001, vol. 197, pp. 3-24.
Sharma, S.T. and Nieman, L.K., "Cushing's Syndrome: All Variants, Detection, and Treatment", Endocrinol Metab Clin North Am, 2011, vol. 40, pp. 379-391.
Smith, K.S. et al., "Reduction of fear-potentiated startle by benzodiazepines in C57BL/6J mice", Psychopharmacology, 2011, vol. 213, pp. 697-706.
Smith, G.D. et al., "Cortisol, Testosterone, and Coronary Heart Disease: Prospective Evidence From the Caerphilly Study", Circulation, 2005, vol. 112, pp. 332-340.
Somers, J. M. et al., "Prevalence and Incidence Studies of Anxiety Disorders: A Systematic Review of the Literature", Can. J. Psychiatry, Feb. 2006, vol. 51, No. 2, pp. 100-113.
Spevack, A.A. et al., "Effect of Amygdalectomy on Habituation and CER in Rats", Physiol. Behav., 1975, vol. 15, pp. 199-207.
Sripada, R.K. et al., "Altered resting-state amygdala functional connectivity in men with posttraumatic stress disorder", J Psychiatry Neurosci, 2012, vol. 37, No. 4, pp. 241-249.

(56) References Cited

OTHER PUBLICATIONS

Starkman, M.N. et al., "Elevated Cortisol Levels in Cushing's Disease Are Associated With Cognitive Decrements", Psychosomatic Medicine, 2001, vol. 63, pp. 985-993.
Steimer, T. "Animal models of anxiety disorders in rats and mice: some conceptual issues", Dialogues Clin Neurosci, 2011, vol. 13, No. 4, pp. 495-506.
Tindle, H.A. et al., "Trends in use of complementary and alternative medicine by US adults: 1997-2002", Alternative Therapies in Health and Medicine, 2005, vol. 11, No. 1, pp. 42-49.
Thomson, F. and Craighead, M., "Innovative Approaches for the Treatment of Depression: Targeting the HPA Axis", Neurochem Res, 2008, vol. 33, pp. 691-707.
Travison, T.G. et al., "Cortisol levels and measures of body composition in middle-aged and older men", Clinical Endocrinology, 2007, vol. 67, pp. 71-77.
Trenzado, C.E., "Physiological changes in rainbow trout held under crowded conditions and fed diets with different levels of vitamins E and C and highly unsaturated fatty acids (HUFA)", Aquaculture, 2008, vol. 277, pp. 293-302.
Walker, D.L. and Davis, M., "Quantifying fear potentiated startle using absolute versus proportional increase scoring methods: implications for the neurocircuitry of fear and anxiety", Psychopharmacology, 2002, vol. 164, pp. 318-328.
Wolkowitz, O.M. et al., "Antiglucocorticoid Treatment of Depression: Double-blind Ketoconazole", Biol Psychiatry, 1999, vol. 45, pp. 1070-1074.

* cited by examiner

PLANT COMPOSITIONS AND METHODS AND USES THEREOF FOR TREATING ELEVATED GLUCOCORTICOID RELATED DISORDERS, AND ANXIETY

RELATED APPLICATIONS

This application is a national phase entry of PCT/CA2013/000950 filed Nov. 8, 2013 (which designates the U.S.) which claims priority to U.S. Provisional Patent Application No. 61/724,381 filed on Nov. 9, 2012, the content of which are incorporated herein by reference in their entirety.

FIELD

The disclosure relates to compositions of members of the Marcgraviaceae family, such as *Souroubea* spp. and members of the Platanaceae family, such as *Platanus* spp., and methods and uses thereof for treating anxiety and elevated glucocorticoids, such as cortisol and corticosterone, elevated adrenocorticotropic hormone (ACTH), related disorders, including stress.

BACKGROUND

There is an ever-increasing interest in herbal or natural-source remedies or medications. Many individuals would rather use such products than conventional pharmaceutical preparations. Additionally, medicinal substances derived from natural products can provide commercial or industrial opportunities for local populations in areas where medicinal plants grow or are cultivated. Moreover, compounds identified as the active ingredients in natural products form an important basis for pharmaceutical research.

Anxiety is a serious disorder that affects many people. Anxiety disorders can be classified into the following sub-categories: generalized anxiety disorder, panic disorders, phobias, obsessive-compulsive disorders, posttraumatic stress disorder, acute stress disorders and anxiety disorders due to medical conditions, substance abuse and not otherwise specified anxiety (American Psychiatric Association. (1994). Diagnostic and statistical manual of mental disorders, 4$^{th}$ Ed. (DSM-IV). Washington, D.C. (DSM-IV). Anxiety disorders are characterized by three basic components; subjective psychological reports, behavioral responses and physiological responses. A person usually reports subjective feelings of tension, apprehension, dread and expectations of an inability to cope (Alloy, L. B., Jacobson, N. S, & Acocella, J., (1999). Abnormal Psychology: Current Perspectives (pp. 150-172.). McGraw-Hill, Boston Mass.). These feelings can lead the person to behavioral responses as coping mechanisms, such as avoidance of the feared situation, impaired speech and motor functioning, and impaired performance on complex cognitive tasks. Physiological changes are often manifested as well; these include muscle tension, increased heart rate and blood pressure, dry mouth, nausea and dizziness (Gray and McNaughton, 2000; Steimer 2011; Edwards 1991).

Marcgraviaceae is a plant family found in the neotropics. WO02/091858 to Durst et al. describes the use of Marcgraviaceae compositions containing betulinic acid, betulinic acid derivatives and uses thereof for treating anxiety.

Platanaceae is a family of large monoecious trees that have the characteristic exfoliating bark and is commonly referred to as the "Plane tree Family or Sycamore Family". As a family, it is represented by a single living genus *Platanus* containing 6-10 species native to the temperate and sub tropical regions of the Northern Hemisphere.

Stress and anxiety are physiologically distinct phenomena that involve different brain regions, signaling systems, signaling molecules and outcomes. The inhibitory neurotransmitter GABA plays a central role in anxiety. Molecules that target receptors and enzymes in the GABA system are used in the pharmacological treatment of anxiety (Durant et al., 2010; Lydiard, 2003). The prevalence of anxiety disorders is widespread globally and afflicts approximately 12% of the world's population (Davidson 2009; Somers et al. 2006; Tindle et al. 2005). The strategies employed for treating these anxiety disorders are strongly influenced by local socio-economical factors and traditional practices. In more developed areas of the world, the most common approach for treating anxiety is pharmacotherapy (Cloos & Ferreira 2009; Sheehan & Sheehan 2007). More specifically, the most widely prescribed drugs for treating anxiety belong to benzodiazepines which are known to act through the GABArergic system (Dinan 2006; Lader 1984). In more recent decades, busiprone which acts primarily through the serotonergic system is also being used (Dinan 2006). Other pharmacological tools to treat anxiety disorders include monoamine oxidase inhibitors (MAOIs), tricyclic antidepressants (TCAs), and serotonin-noradrenaline re-uptake inhibitors (SSRI) (Baldwin & Polkinghorn 2005; Sheehan & Sheehan 2007b).

In the vertebrates, the perception of stress initiates a response cascade involving the hypothalamus-pituitary-adrenal (HPA, in mammals) or interrenal (HPI, in fish) axis. The HPA or HPI axis is a major part of the neuroendocrine system that controls reactions to stress and regulates many body processes. When stress is perceived, responses occur in these stress axes, which stimulates the release of corticotrophin-releasing-factor (CRF) from the hypothalamus. This in turn stimulates the release of adrenocorticotropic hormone (ACTH) from the pituitary gland. ACTH circulates in the blood and stimulates the release of cortisol (corticosterone in rodents) from the adrenal cells (or head kidney cells in fish) into the blood stream. Cortisol is the primary signaling molecule in the HPA axis. Cortisol levels are elevated in animals in response to stress, which leads to physiological changes that can help the animal respond to stress, for example by an enhanced flight or fight response. Cortisol mediates a host of physiological response such as increased catabolism, aggression and down regulation of other functions such as immune responses and reproduction function in mammals. In stress trials, circulating plasma cortisol (corticosterone) is considered a common biomarker to confirm that a stimulus exerts significant stress and to distinguish non-stressed from stressed animals (Gamperl et al., 1994).

These responses are thought to be a short term biological adaptation to stress in animals, however, chronic stress, which can lead to chronically elevated cortisol, hypercortisolism, is maladaptive, and is implicated in disease in both animals and humans. In livestock, elevated stress slows growth and reduces production (Rostagno, 2009). Stress is a concern in aquaculture. The stress response in fish leads to mobilization of energy-rich substrates by depletion of hepatic glycogen stores, elevation of plasma glucose, changes in circulating free fatty acid levels and general inhibition of protein synthesis. These responses have a catabolic effect on fish. Therefore in aquaculture, elevated cortisol adversely affects growth rate, immunity and reproduction (Schreck et al., 2001). In animal production in agriculture, juvenile pigs experience stress when weaned and moved into common pens, elevating cortisol. As a result of their elevated cortisol, they have lower weight gain and their high aggression and lower immune function leads to fights, injuries and more infections. In humans, stress and stress-related illnesses are widespread among people and increasingly a link has been identified between elevated plasma cortisol levels and heart disease, obesity, metabolic syndrome, hyperglycermia (Brown D F et al., 2003). Hypercortisolemia is associated with severe bone loss and depression in hypothalamic Amenorrhea and Anorexia Nervosa (Lawson et al. 2009) and depression (Anagnostis et al., 2009; Carroll et al., 2007; Gathercole and Stewart, 2010; Smith et al., 2005 Parker et al., 2003). In humans, diverse stressful stimuli, including low socioeconomic status, race (Hajat et al., 2010), chronic work stress (Chandola et al., 2006), anxiety and depression (Carroll et al., 2007) stimulate neuroendocrine responses. Pain caused by muscular problems (tension headaches, back and jaw pain, repetitive stress syndrome), gastrointestinal disorders (heart burn, diarrhea, stomach pain) (Anagnostis 2009), mental disorders (eating disorders, anxiety, depression, schizophrenia, insomnia, substance abuse) (Parker, 2003) can also stimulate neuroendocrine responses. Stress related behavior (for example cowering, licking, circling, digging and chewing in dogs) when facing a stressful stimuli such as, transportation, veterinarian visits, vaccination and drug treatments can also result in a neuroendocrine response (Herron, 2008). Animals raised in large scale industrial farms are housed in an environmentally stressful context and express high levels of glucocorticoids, resulting in reduced reproductive efficiency and limited yield in overall productivity.

Notwithstanding the link between hypercortisolism and a variety of human illnesses, pharmacological treatments for hypercortisolism are still under investigation. The hypercortisolism present in Cushing's syndrome is typically caused by a tumor (adrenal or pituitary) and treated with surgery (Sharma and Nieman, 2011). The interest in the role of hypercortisolism in metabolic syndrome stems from the phenotypic similarities between patients with Cushing's and metabolic syndrome. Both include central obesity, impaired glucose tolerance, insulin resistance, type-two diabetes, increased cardiac risk of mortality, osteoporosis and depression (Gathercole and Stewart, 2010). Normalizing cortisol levels usually reverses the symptoms in Cushing's syndrome (Stewart, 2003).

Stress and stress-related illness is widespread, and links between elevated plasma cortisol and heart disease (Smith at al., 2005), obesity (Travison et al., 2007) and depression (Carroll at al., 2007; Parker et al., 2003) have been reported. Aberrations in HPA axis function, including hypercortisolism, are strongly associated with depression (Gallagher at al., 2008). Drugs that inhibit cortisol synthesis, including ketoconazole, aminoglutethimide and metyrapone, have been examined for their therapeutic potential in treating depression (Kling et al., 2009; Starkman et al., 2001) and have shown some promise in bipolar patients with depressive symptoms (ketoconazole) (Brown et al., 2001), and patients with major depressive disorder (MDD). In a blind, placebo-controlled study with patients suffering from MDD, co-delivery of metyrapone (an inhibitor of cortisol synthesis by blocking the mitochrondrial steroidogenic enzyme steroid 11-β hydroxylase) and a standard serotonergic antidepressant (nefazodone or fluvoxamine), significantly reduced depression (50% reduction in HAM-D scores at day 35 of treatment) (Jahn et al., 2004). However, despite the potential of cortisol-lowering drugs to treat depression, they are also associated with serious side-effects (Thomson and Craighead, 2008), including ketoconazole's potential for liver toxicity (Kim et al., 2003) and strong inhibition of cytochrome P450 3A (Cook et al., 2004), with the consequence that in some clinical trials up to 20% of patients drop out due to the side-effects (Wolkowitz et al., 1999).

In the context of metabolic syndrome, inhibition of the enzyme 11β hydroxysteroid dehydrogenase 1 (11-β HSD1) to treat hypercortisolism has been examined (Gathercole and Stewart, 2010). At the pre-receptor level, 11-β HSD1 converts metabolically inactive cortisone to active cortisol (11-dehydrocorticosterone to corticosterone in rodents). In rodent models of metabolic syndrome, inhibition of 11-β HSD1 improves metabolic profile (Gathercole and Stewart, 2010). A recent Phase I clinical trial with a selective 11-β HSD1 inhibitor shows good tolerability and no activation of the HPA axis in healthy patients (Courtney et al., 2008).

Post Traumatic Stress Disorder (PTSD) is an anxiety disorder that results from exposure to a traumatic event. The disabling psychological symptoms associated with PTSD can occur long after the exposure to the traumatic event(s). The DSM-V encompasses several symptoms related to the disorder, including numbing, avoidance, increased arousal and it is often associated re-experiencing of the past trauma. PTSD symptoms elicit severe distress and/or impair normal functioning. PTSD has become a global health issue, with prevalence rates ranging from 1.3% to 37.4%. As PTSD is often accompanied with other health conditions, it is difficult to appropriately pinpoint a specific treatment regimen for each individual of them. Serotonin reuptake inhibitors (SSRIs) or serotonin/norepinephrine reuptake inhibitors (SNRIs) and benzodiazepines, are typically used to treat PTSD. However, the outcomes are variable, as majority of affected individuals do not experience full remission. Furthermore, there are a number of side effects (e.g. sedation, decreased libido, weight gain) with these drugs. The usage of anxiolytic plants for treating the symptoms associated with PTSD has been suggested by Maddox et al. (2013), Passie et al. (2012) and Sarris et al. (2013).

Conditioned fear is relevant to Post Traumatic Stress Disorder. Pavlovian fear conditioning (FC) is an important paradigm for studying memory processes and related brain circuits that are relevant to PTSD (Cain et al., 2012; Parson et al. 2013). Models of FC in rodents include conditioned emotional response (CER) and fear potentiated startle paradigm (FPS). FC occurs when a neutral stimulus (e.g. light or tone) is conditioned (CS) or temporally paired with naturally aversive unconditioned stimuli (US; foot shock). Typically, after a number of repeated pairings, the CS itself acquires the capacity to elicit responses akin to that of US, that is a fear response. Thus, FC is an extremely powerful form of associative learning; if the CS is sufficiently salient and the US sufficiently aversive, even a single brief episode can lead to strong fear memories that can last a lifetime. FC studies have greatly enhanced our understanding of the neurobiology of memory and emotional responding. Although FC does not necessarily produce PTSD, psychological and neural processes mediating FC likely engage brain circuits and processes that contribute to PTSD. FC has several important features and phases that may make distinct contributions to PTSD or treatment (Cain et al., 2012; Parson et al. 2013).

Acquisition refers to the process by which the organism learns that the conditioned stimulus predicts the unconditioned stimulus. Treatments that block the acquisition of fear conditioning are applied before CS-US pairings and prevent the development of short-term memory (STM) memory, tested within a few hours, and consequently the formation of long-term memory (LTM), tested many hours or days later.

The consolidation of fear conditioning refers to the transformation of the short-term memory from a labile state immediately after acquisition to a more permanent state with the passage of time. Treatments that disrupt the consolidation of memory are usually applied a few minutes to a few hours after CS-US pairings, leaving STM intact but resulting in LTM disruption.

Retrieval (also refers to as expression) refers to the conditioned responding that occurs after CS-US relationship has been established. Retrieval is assessed by presenting the CS alone and then measuring the conditioned response. Treatments that disrupt retrieval are typically administered shortly before the conditioned response is assessed. Drugs that disrupt retrieval may blunt PTSD symptoms.

PTSD research has been focused on two other phases on CF, namely reconsolidation and extinction. Reconsolidation occurs after retrieval. During a brief window of time after the retrieval of the fearful memories, the specific memory and its association with an emotional response, return to an unstable state, during which time the "repackaging" of the memory is vulnerable to pharmacological intervention. Reconsolidation of memory is considered to be disrupted when a drug is applied shortly after retrieval and leaves STM intact yet disrupts LTM.

SUMMARY

The present inventors have demonstrated that a composition comprising extracts of both *Souroubea* and *Platanus* species provides anxiolytic activity attributable to more than the betulinic acid content within the extracts. Accordingly, the present disclosure provides a composition comprising A) a preparation obtained from a plant species of the family Marcgraviaceae and B) a preparation obtained from a plant species of the family Platanaceae. In one embodiment, the ratio of A:B ranges from 1:99 to 99:1, optionally from 15:85 to 85:15 or from 20:80 to 80:20 or from 30:70 to 70:30 or from 40:60 to 60:40. In a particular embodiment, the ratio of A:B is 25:75, 55:45, 50:50 or 75:25.

In an embodiment, the composition further comprises a carrier, such as a pharmaceutically acceptable carrier.

In another embodiment, the betulinic acid (BA) marker content of the composition is such that it results in a BA concentration of 0.05 mg/kg to 800 mg/kg. When given to an animal, including human, the dose level of the BA is in the range of 0.1 mg/kg to 25 mg/kg, optionally about 1 mg per kg of body weight per day to about 2.5 mg/kg of body weight per day.

In an embodiment, the plant of the family Marcgraviaceae is of the genus *Souroubea*, such as, but not limited to, *Souroubea gilgii, Souroubea sympetala, Souroubea loczyi, Souroubea venosa, Souroubea vallicola, Souroubea guianensis, Souroubea swartzi* or a combination thereof.

In another embodiment, the plant of the family Platanaceae is of the genus *Platanus*, such as *Platanus occidentalis, Platanus orientalis Platanus acerfolia, Platanus chiapensis, Platanus oaxacan, Platanus gentryi, Platanus zedowski, Platanus hybrid, Platanus racemosa, Platanus wrightii* or a combination thereof. In a particular embodiment, the *Platanus* plant is a *Platanus occidentalis, Platanus acerfolia* or a combination thereof, such as, but not limited to, as a 90:10 to 10:90 combination of *Platanus occidentalis* and *Platanus acerfolia*.

In another embodiment, the composition further comprises an additional anxiolytic agent or glucocorticoid decreasing agent.

Also provided herein is a commercial package comprising a composition disclosed herein and instructions for use in treating anxiety, stress and/or a glucocorticoid-related condition in a subject.

Further provided herein is a method of treating anxiety comprising administering a composition disclosed herein to an animal in need thereof. Also provided is use of a composition disclosed herein for treating anxiety in an animal in need thereof. Even further provided is use of a composition disclosed herein in the preparation of a medicament for treating anxiety in an animal in need thereof. Also provided is a composition disclosed herein for use in treating anxiety in an animal in need thereof.

In an embodiment, the animal has Post Traumatic Stress Disorder.

The present inventors have also demonstrated that Marcgraviaceae extracts and/or Platanaceae extracts are able to reduce cortisol levels and this is attributable to more than the betulinic acid content.

Accordingly, further provided herein is a method of treating stress comprising administering a composition disclosed herein or a preparation of Marcgraviaceae and/or Platanaceae to an animal in need thereof. Also provided is use of a composition disclosed herein or a preparation of Marcgraviaceae and/or Platanaceae for treating stress in an animal in need thereof. Even further provided is use of a composition disclosed herein or a preparation of Marcgraviaceae and/or Platanaceae in the preparation of a medicament for treating stress in an animal in need thereof. Also provided is a composition disclosed herein or a preparation of Marcgraviaceae and/or Platanaceae for use in treating stress in an animal in need thereof.

In an embodiment, the preparation is an extract.

Even further provided herein is a method of reducing elevated glucocorticoid, such as cortisol or corticosterone, comprising administering a composition disclosed herein or a preparation of Marcgraviaceae and/or Platanaceae to an animal in need thereof. Also provided is use of a composition disclosed herein or a preparation of Marcgraviaceae and/or Platanaceae for reducing elevated glucocorticoid, such as cortisol or corticosterone, in an animal in need thereof. Even further provided is use of a composition disclosed herein or a preparation of Marcgraviaceae and/or Platanaceae in the preparation of a medicament for reducing elevated glucocorticoid, such as cortisol or a corticosterone, in an animal in need thereof. Also provided is a composition disclosed herein or a preparation of Marcgraviaceae and/or Platanaceae for use in reducing elevated glucocorticoid, such as cortisol or corticosterone, in an animal in need thereof.

In one embodiment, the methods and uses for reducing elevated glucocorticoid, such as cortisol or corticosterone, are useful in the treatment of an elevated glucocorticoid-related condition, such as but not limited to maintain bone density, to maintain and improve the immune system, to treat Cushing's syndrome, to treat obesity, to control weight gain, to improve reproduction efficiency, to reduce aggression and hyperactivity, to treat metabolic disorder, to treat hypertension, to treat hyperglycemia, to treat insulin resistance, to treat type 2 diabetes, and/or to aid in cancer and immune therapies. In another embodiment, the glucocorticoid related condition is stress related or results in stress.

In one embodiment, the animal is human, horse (equine), pig (susidae), sheep, goat, farmed fish (e.g. salmonids, catfish etc.) or crustacean (e.g. shrimp, prawns), bird (e.g. turkeys, fowls, chickens), cattle, endangered or captive species (e.g. zoo animal or aquarium animal) or pet animal (e.g. dog (canine), cat (feline)). In another embodiment, the animal is a human.

The compositions disclosed herein or preparations disclosed herein may be administered in any manner, such as, sublingually, orally, parenterally, intravenously, topically, intraperitoneally, or rectally.

In one embodiment, a composition disclosed herein or a preparation of Marcgraviaceae and/or Platanaceae may be administered or used prophylactically in advance of an anticipated anxiety, stress or elevated glucocorticoid-related condition. In an embodiment, the anticipated anxiety is when the subject is facing an event that has previously triggered anxiety or is reasonably anticipated to trigger anxiety.

In another embodiment, the methods and uses disclosed herein further comprise administering or using at the same time or sequentially an additional therapeutic, such as, but not limited to, an anxiolytic agent, glucocorticoid decreasing agent, chemotherapeutic, insulin, tranquilizer, or other diabetic therapy.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

Figure 1:
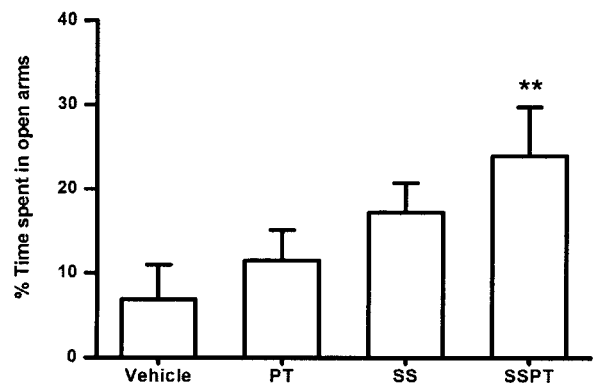
FIG. 1 shows (A) the percentage of time the rats, spent in the open arms and (B) the number of unprotected head dips on the elevated plus maze following three consecutive daily oral administrations of treatment. ** $p<0.01$ indicates a significant difference from vehicle. *Souroubea gilgii* (SS), *Platanus occidentalis* (PT), the combination of *Souroubea gilgii* and *Platanus occidentalis* in a ratio of SS 55% to PT 45%, (SSPT), and Vehicle control.
Figure 1:
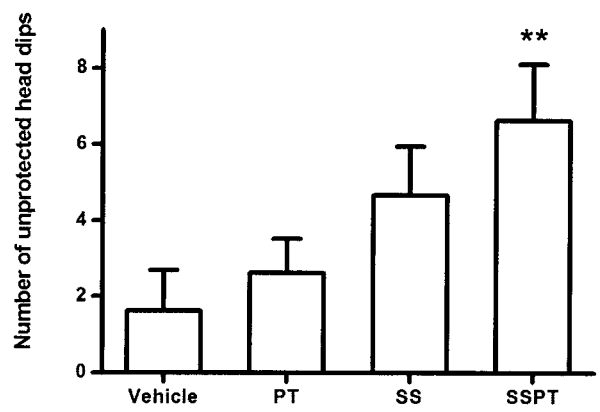

The present inventors have demonstrated that a blend of *Souroubea* species (SS) and *Platanus* species (PT) plant preparations unexpectedly resulted in a synergistic alleviation of anxiety and fear responses compared to either preparation alone. In addition to its effect on the anxiety response, the plant preparations also had the effect of reducing cortisol. Reduction of cortisol is useful for treatment of many conditions related to elevated levels of cortisol. Anxiety and stress have different core pharmacologies. In anxiety, the GABAergic system is involved and typically is treated via $GABA_A$ receptor agonists. Stress involves cortisol biosynthesis and activation of the glucocorticoid receptor. Although the two conditions can be interconnected in subjects, they are separate independent events.

Compositions

Accordingly, the present disclosure provides a composition comprising A) a preparation obtained from a plant of the family Marcgraviaceae and B) a preparation obtained from a plant of the family Platanaceae.

The term "plant" as used herein encompasses whole plants or plant parts, including without limitation, plant cells, tissues, seeds, embryos, roots, leaves, bark, stems, vines, fruits and flowers.

The term "preparation" as used herein refers to a non-naturally occurring composition of matter that contains more or less than the entire complement of biological materials found in either plant (entire plant or plant parts) alone or an extract of a plant or plant part. In this respect, a composition comprising the combination of plant or plant materials from more than one plant species or a composition from which some or all of the moisture, fiber and/or carbohydrates are separated (such as bale) would constitute a "preparation" as would whole plant or combination plant materials that have been ensiled (fermented).

For example, baled material must be field dried or kiln dried from greater than 90% moisture content (fresh plant material) to approximately 25% (or lower (15%)) moisture prior to baling. Baled plant materials have much lower moisture content than the original plant materials. Baled product that is not dried sufficiently is subject to the growth of moulds that would cause putrefaction of the plant material. Ensiling is a fermentation process whereby plants are stored and compacted to allow plant sugars to be fermented by anaerobic bacteria to organic acids, which then reduce the pH of the plant material. This process preserves the crop during long-term storage. The end product is called 'silage' or 'ensilage'.

Accordingly, in one embodiment, the preparation comprises a tea-like beverage (infusion or decoction) made by steeping or boiling the plant leaves in hot water and then removing the leaves. In another embodiment, the preparation comprises a dried, finely ground powder of the plant(s). The powder would have a moisture content far below that found in nature.

In yet another embodiment, the plant preparation is an extract obtained by contacting the Marcgraviaceae plant material or Platanaceae plant material, such as fruit, leaves, other plant parts or mixtures thereof, with a solvent to form an extract, and then recovering the extract. In one embodiment, the solvent is other than water. In another embodiment, the solvent is ethanol, ethyl acetate, dichloromethane, Supercritical $CO_2$ or any combination thereof. In an embodiment, the solvent is form 20 to 95% ethanol.

In yet a further embodiment, the plant preparations are prepared by grinding the material to a fine powder and then blending together. After blending, the preparations are optionally dry heat sterilized or gamma irradiated to control the microbiological load inherent with field collected materials. The plant materials alone or in combination may be ground to various mesh sizes depending on how they are subsequently processed. In some cases the materials are made into fine four(s) (30 to 80 mesh) that can be used for tablets. In other cases they are left a little coarser (10-30 mesh) and used in extractions.

The preparation may be concentrated to varying degrees, limited principally by the amount of plant material a subject can conveniently ingest. Generally, the preparation has been separated from at least the fibrous plant material and the naturally-occurring woody lignified cellulosic plant materials.

All members of the family Marcgraviaceae have similar phytochemical components and are useful in the present disclosure, including without limitation, *Souroubea, Schwartzia, Macgraviastrum, Norantea, Ruyschia* and *Sarcopera*. Optionally, the plants are of the genera *Souroubea* or *Schwartzia*.

In one embodiment, the plant of the family Marcgraviaceae is of the genus *Souroubea*. Plants of the *Souroubea* genus include, without limitation, *Souroubea gilgii* V. A. Richt (synonym *Souroubea belizensis* Lundell), *Souroubea sympetala* Gigli (synonyms *Souroubea guianensis* Aubl.; *Ruyschia quianensis* (Aubl.) Sw.), *Souroubea loczyi* de Roon, *Souroubea venosa* Shery, *Souroubea vallicola, Souroubea guianensis* Woodson, *Souroubea swartzi* or a combination thereof.

In an embodiment, the *Souroubea* plant is *Souroubea sympetala* or *Souroubea gilgii*. *Souroubea sympetala* is a Neotropical vine that is indigenous to Guatemala, Belize, Nicaragua, Costa Rica, Panama, Colombia, Venezuela, and Peru. *Souroubea gilgii* is a Mesoamerican vine indigenous to Guatemala, Belize, Nicaragua, Costa Rica, and Panama.

All members of the family Platanaceae have similar phytochemical components and are useful in the present disclosure, including without limitation, the genus *Platanus*.

Accordingly, in one embodiment, the plant of the family Platanaceae is of the genus *Platanus*. *Platanus* is a genus of trees that grow as native species in the northern hemisphere (family Platanaceae). Plants of the *Platanus* genus include, without limitation, *Platanus occidentalis, Platanus acerfolia, Platanus chiapensis, Platanus oaxacan, Platanus gentryi, Platanus zedowski, Plantanus orientalis, Platanus hybrid, Platanus racemosa, Platanus wrightii* or a combination thereof.

*Platanus occidentalis* is commonly referred to as the American Sycamore, American Plane, Buttonwood, or, Occidental Plane. This tree is native to North America, and is distributed across the eastern United States and southwestern Ontario. Its range extends from Iowa through Ontario to Maine in the north, Nebraska in the west, and Texas and Florida in the south. This species has been hybridized with the European species, *P. orientalis*, to produce the London Plane tree, *Platanus acerifolia*, which is a pollution tolerant tree, widely planted in boulevards of European cities. The American sycamore tree has blotchy, exfoliating bark, that peels off in large quantities. The reason for this is the tissue of the bark is very rigid in texture compared to other trees, and lacks the elasticity to allow it to stretch as the tree grows.

Accordingly, in another embodiment, the *Platanus* plant is a *Platanus occidentalis, Platanus acerfolia* or a combination thereof. In an embodiment, the Platanaceae preparation comprises a combination of *Platanus occidentalis* and *Platanus acerfolia*.

The ratio of A) the plant preparation from Marcgraviaceae to B) the plant preparation from Platanaceae depends on the formulation and intended subject. A mixture of Marcgraviaceae (e.g. *souroubea*) and Platanaceae (e.g. sycamore) material is better than the Platanaceae material alone or the Marcgraviaceae material on its own.

One way to standardize the blends from different species is done using a blend of the plant preparations with a consistent amount of betulinic acid, as a marker. In one embodiment, the amount of A:B provides a total betulinic acid (BA) concentration of 0.05 mg/kg to 800 mg/kg. When given to an animal, including human, the dose level of BA is in the range of 0.1 mg/kg to 25 mg/kg body weight per day, optionally about 1 mg/kg body weight per day to about 2.5 mg/kg of body weight per day.

The term "betulinic acid" as used herein refers to a powder, having a molecular weight of 456.71, a melting point of 316-318° C. and an empirical formula of $C_{30}H_{50}O_2$. The structural formula of betulinic acid is:

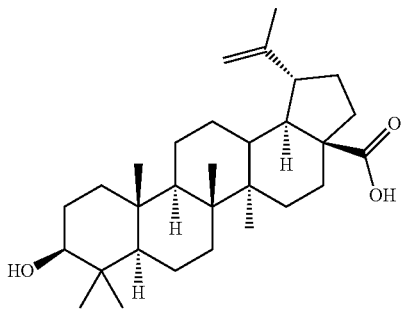

In one embodiment, the ratio of A:B is from 1:99 to 99:1. In another embodiment, the ratio of A:B is from 15:85 to 85:15 or 20:80 to 80:20 or 30:70 to 70:30. In yet another embodiment, the ratio of A:B is from 40:60 to 60:40, optionally 25:75, 55:45, 50:50 or 75:25.

The compositions as disclosed herein or the preparations as disclosed herein may be incorporated into a pharmaceutical composition, or into a supplement, such as a nutritional supplement, a food product, a beverage or the like, as known in the art.

Accordingly the compositions disclosed or preparations disclosed herein further comprise a carrier.

In one embodiment, the composition or preparation is a pharmaceutical composition and the carrier is a pharmaceutically acceptable carrier, diluent or excipient.

The pharmaceutical compositions can be prepared by per se known methods for the preparation of pharmaceutically acceptable compositions which can be administered to patients, and such that an effective quantity of the active ingredients is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 2003—20$^{th}$ Edition) and in The United States Pharmacopeia: The National Formulary (USP 24 NF19) published in 1999).

The pharmaceutical compositions may additionally contain other agents such as those disclosed herein as additional anxiolytic agents or glucocorticoid decreasing agents.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The pharmaceutical composition may be supplied, for example but not by way of limitation, as a lyophilized powder which is reconstituted with sterile water or saline prior to administration to the patient.

Suitable carriers include, without limitation, fillers, such as sugars, for example lactose, saccharose, mannitol or sorbitol, cellulose preparations and/or calcium phosphates, for example tricalcium phosphate or calcium hydrogen phosphate, also binders, such as starch pastes, using, for example, corn, wheat, rice or potato starch, gelatin, gum tragacanth, methyl-cellulose and/or polyvinylpyrrolidone, and if desired, disintegrators, such as the above-mentioned starches, also carboxymethyl starch, cross-linked polyvinylpyrrolidone, agar or alginic acid or a salt thereof, such as sodium alginate, vegetable oils, gums, methyl cellulose, PVP, cyclodextrose, maltodextrose, flavoring agents, flavored powders, smoothies, gels etc.

Suitable excipients include, without limitation, flow conditioners and lubricants, for example, silicic acid, talc, stearic acid or salts thereof, such as magnesium or calcium stearate, and/or polyethylene glycol. Dragee cores are provided with suitable coatings that may be resistant to gastric juices, there being used, inter alia, concentrated sugar solutions which may contain gum Arabic, talc polyvinylpyrrolidone, polyethylene glycol and/or titanium dioxide, coating solutions in suitable organic solvents or solvent mixtures, or, for the preparation of enteric coatings, solutions of suitable cellulose preparations, such as acetylcellulose phthalate or hydroxypropylmethylcellulose phthalate or microcrystalline cellulose. Colourings or pigments may be added to the tablets or dragee coatings, for example for identification purposes or to indicate different doses of active ingredient.

Further orally administrable pharmaceutical compositions include dry-filled capsules consisting of gelatin, and also soft sealed capsules consisting of gelatin and a plasticizer, such as glycerol or sorbitol. The dry-filled capsules may contain the active ingredients in the form of granules, for example, in admixture with fillers, such as lactose, binders, such as starches, and/or glidants, such as talc or magnesium stearate, and optionally stabilizers. In soft capsules, the active ingredients may be dissolved or suspended in suitable liquids such as fatty oils, paraffin oil or liquid polyethylene glycols, to which stabilizers may be added.

Rectally administrable pharmaceutical compositions, for example, suppositories that comprise a combination of the active ingredients and a suppository base are also provided. Suitable as suppository bases are, for example, natural or synthetic triglycerides, paraffin hydrocarbons, polyethylene glycols and higher alkanols. It is also possible to use gelatin rectal capsules that comprise a combination of the active ingredients and base material. Suitable base materials are, for example, liquid triglycerides, polyethylene glycols and paraffin hydrocarbons. Administration of an "effective amount" of the compositions in the methods and uses of the present disclosure is defined as an amount effective, at dosages and for periods of time necessary to achieve the desired result.

The compositions disclosed herein may also be administered parenterally. Solutions can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. Conventional procedures and ingredients for the selection and preparation of suitable formulations are described, for example, in Remington's Pharmaceutical Sciences (2000-20th edition) and in The United States Pharmacopeia: The National Formulary (USP 24 NF19) published in 1999.

The pharmaceutical forms suitable for injectable use include sterile aqueous solutions or dispersion and sterile powders for the extemporaneous preparation of sterile injectable solutions or dispersions. In all cases, the form must be sterile and must be fluid to the extent that easy syringability exists.

Compositions suitable for buccal or sublingual administration include tablets, lozenges, and pastilles, wherein the active ingredient is formulated with a carrier such as sugar, acacia, tragacanth, or gelatin and glycerine.

The dosage of the compositions disclosed herein can vary depending on many factors such as the pharmacodynamic properties of the active ingredients, the mode of administration, the age, health and weight of the recipient, the nature and extent of the symptoms, the frequency of the treatment and the type of concurrent treatment, if any, and the clearance rate of the composition in the animal to be treated. One of skill in the art can determine the appropriate dosage based on the above factors. The compositions disclosed herein may be administered initially in a suitable dosage that may be adjusted as required, depending on the clinical response. As a representative example suitable for animals, oral dosages of a composition based on the marker assay of Betulinic Acid (BA) concentration will range between about 0.1 mg/kg of body weight per day to about 25.0 mg/kg body weight per day for an adult, more suitably about 1 mg/kg of body weight per day to about 2.5 mg/kg of body weight per day. When formulated for oral administration to animals, the compositions for example, are suitably in the form of tablets containing 0.1, 1, 5, 10, 20, 40, 80, 100, 200, 300, 400 or 800 mg of active ingredient per tablet. The compositions may be administered in a single daily dose or the total daily dose may be divided into two, three of four doses.

The mode of administration (e.g. in vivo by injection) will also impact the dosage regimen. For example, if the compositions are to be administered transdermally, using, for example, those forms of transdermal skin patches that are well known to those skilled in the art, the dosage administration will be continuous rather than intermittent throughout the dosage range.

In another embodiment, the compositions disclosed herein further comprise an additional active ingredient, such as an additional anxiolytic drug such as, but not limited to, benzodiazepine or buspirone or an additional glucocorticoid decreasing agent such as, but not limited to, ketoconazole, aminoglutethimide and metyrapone.

In an embodiment, the carrier is a binder, such as but not limited to microcrystalline cellulose, and other binders commonly known to the person skilled in the art.

Methods and Uses

In another aspect, the present disclosure provides a method of treating anxiety comprising administering a composition of a preparation obtained from a plant of the family Marcgraviaceae and B) a preparation obtained from a plant of the family Platanaceae as disclosed herein to an animal in need thereof. Also provided herein is use of a composition of a preparation obtained from a plant of the family Marcgraviaceae and B) a preparation obtained from a plant of the family Platanaceae as disclosed herein for treating anxiety in an animal in need thereof. Further provided is use of a composition of a preparation obtained from a plant of the family Marcgraviaceae and B) a preparation obtained from a plant of the family Platanaceae as disclosed herein in the preparation of a medicament for treating anxiety in an animal in need thereof. Even further provided is a composition of a preparation obtained from a plant of the family Marcgraviaceae and B) a preparation obtained from a plant of the family Platanaceae as disclosed herein for use in treating anxiety in an animal in need thereof.

The term "anxiety" as used herein refers to both acute and chronic anxiety, including without limitation, symptoms associated with generalized anxiety disorder, panic disorder, phobias, such as agoraphobia, social anxiety disorder, obsessive compulsive disorder, post-traumatic stress disorder, separation anxiety, weaning anxiety, noise anxiety (eg. Thunderstorms, fireworks), conditioned anxiety (such as transportation, visiting the veterinarian or doctor, use of restraints, meeting new animals or humans) and exposure anxiety. The phrase "treating anxiety" as used herein refers to treating, delaying or inhibiting at least one sign or symptom of anxiety.

Symptoms of anxiety include, without limitation, a negative or autonomic type of anxiety which can manifest in a number of ways such as a decrease in activity (e.g. freezing, hiding), lowered body posture (crouching, animal having a tail between legs), autonomic or conflict (e.g. panting, trembling, yawning, licking lips); a positive or increased type of anxiety which can manifest in a number of ways such as startle or visual scan and an active response (pacing, aimless activity, repetitive activity, retreating and/or digging) (Steimer 2011). Typical symptoms of anxiety in humans include excessive and ongoing worry, irritability, muscle tension, headaches, sweating, difficulty concentrating, nausea, the need to go to the bathroom frequently, tiredness, trouble failing or staying asleep, trembling, and being easily startled (Wikipedia, see world wide web at en.wikipedia.org/wiki/Anxiety).

For example, pet owners would be familiar with the symptoms of anxiety such as abnormal defecation or urination, barking, howling, destruction of furniture, panting, hiding, nipping, rapid eye movement, crowding and clinging, and fear.

In humans anxiety is very complex and takes several forms: phobia, social anxiety, obsessive-compulsive, and post-traumatic stress. The physical effects of anxiety may include heart palpitations, tachycardia, muscle weakness and tension, fatigue, nausea, chest pain, shortness of breath, headache, stomach aches, or tension headaches. As the body prepares to deal with a threat, blood pressure, heart rate, perspiration, blood flow to the major muscle groups are increased, while immune and digestive functions are inhibited (the fight or flight response). External signs of anxiety may include pallor, sweating, trembling, and pupillary dilation. For someone who suffers anxiety this can lead to a panic attack.

The behavioral effects of anxiety may include withdrawal from situations which have provoked anxiety in the past. Anxiety can also be experienced in ways which include changes in sleeping patterns, nervous habits, and increased motor tension like foot tapping.

The inventors have shown that disruption of reconsolidation ultimately weakens conditioned responding and may be of therapeutic relevance to PTSD. Fear extinction refers to the decrease in fear responses during repeated presentations of the CS without the US. This is thought to be a new form of learning where a new a new inhibitory "CS-No US" memory is formed. Pharmacological approaches that enhance fear extinction are being evaluated for treatment efficacy in PTSD. The inventors have demonstrated that raw material combination and/or extracts of Marcgraviaceae and *Platanus* species disrupt reconsolidation and decrease fear responses in animal models for human PTSD.

Accordingly, in an embodiment, the present disclosure provides a method of treating post traumatic stress disorder (PTSD) comprising administering a composition of a preparation obtained from a plant of the family Marcgraviaceae and B) a preparation obtained from a plant of the family Platanaceae as disclosed herein to an animal in need thereof. Also provided herein is use of a composition of a preparation obtained from a plant of the family Marcgraviaceae and B) a preparation obtained from a plant of the family Platanaceae as disclosed herein for treating PTSD in an animal in need thereof. Further provided is use of a composition of a preparation obtained from a plant of the family Marcgraviaceae and B) a preparation obtained from a plant of the family Platanaceae as disclosed herein in the preparation of a medicament for treating stress in an animal in need thereof. Even further provided is a composition of a preparation obtained from a plant of the family Marcgraviaceae and B) a preparation obtained from a plant of the family Platanaceae as disclosed herein for use in treating PTSD in an animal in need thereof.

The present inventors have also demonstrated that extracts of plants from the Marcgraviaceae family and of the Platanaceae family are able to lower cortisol (or corticosterone) in addition to their anxiolytic activity.

Accordingly in another aspect, the present disclosure provides a method of treating stress comprising administering a composition of a preparation obtained from a plant of the family Marcgraviaceae and B) a preparation obtained from a plant of the family Platanaceae as disclosed herein or a preparation of Marcgraviaceae and/or Platanaceae to an animal in need thereof. Also provided herein is use of a composition of a preparation obtained from a plant of the family Marcgraviaceae and B) a preparation obtained from a plant of the family Platanaceae as disclosed herein or a preparation of Marcgraviaceae and/or Platanaceae for treating stress in an animal in need thereof. Further provided is use of a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for treating stress in an animal in need thereof. Even further provided is a composition of a preparation obtained from a plant of the family Marcgraviaceae and B) a preparation obtained from a plant of the family Platanaceae as disclosed herein or a preparation of Marcgraviaceae and/or Platanaceae for use in treating stress in an animal in need thereof.

In yet another aspect, the present disclosure provides a method of reducing elevated glucocorticoid, such as cortisol or corticosterone, comprising administering a composition of a preparation obtained from a plant of the family Marcgraviaceae and B) a preparation obtained from a plant of the family Platanaceae as disclosed herein or a preparation of Marcgraviaceae and/or Platanaceae to an animal in need thereof. Also provided herein is use of a composition of a preparation obtained from a plant of the family Marcgraviaceae and B) a preparation obtained from a plant of the family Platanaceae as disclosed herein or a preparation of Marcgraviaceae and/or Platanaceae for reducing elevated glucocorticoid, such as cortisol or corticosterone, in an animal in need thereof. Further provided is use of a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for reducing elevated glucocorticoid, such as cortisol or corticosterone, in an animal in need thereof. Even further provided is a composition of a preparation obtained from a plant of the family Marcgraviaceae and B) a preparation obtained from a plant of the family Platanaceae as disclosed herein or a preparation of Marcgraviaceae and/or Platanaceae for use in reducing elevated glucocorticoid, such as cortisol or corticosterone, in an animal in need thereof.

The term "reducing glucocorticoid" as used herein refers to the lowering of the level of glucocorticoid, such as cortisol or corticosterone, circulating in the animal compared to an untreated control. In an embodiment, the glucocorticoid is lowered by 10%, 20%, 30%, 50%, 75%, or more compared to the control glucocorticoid levels. A control can be an untreated animal or a reference standard.

The term "glucocorticoid" as used herein refers to predominant glucocorticoid affecting the animal, such as cortisol or corticosterone. The predominant glucocorticoid in humans (and most mammals and fish) is cortisol (hydrocortisone) whereas corticosterone is the common glucocorticoid in rodents. All animals produce both hormones. Corticosterone is the precursor of the mineralocorticoid, aldesterone.

Reduction of glucocorticoids, such as cortisol/corticosterone, provides a number of benefits to an animal. The methods and uses for reducing glucocorticoid are useful for treating glucocorticoid-related conditions. The term "glucocorticoid-related condition" as used herein refers to any condition that is caused by or affected negatively by an increase in glucocorticoid levels, such as cortisol or corticosterone levels, compared to an unaffected or healthy subject. Accordingly, in an embodiment, the methods and uses for reducing glucocorticoid are used to treat a glucocorticoid-related condition, including without limitation, maintaining bone density, maintaining and improving the immune system, treating Cushing's syndrome, reducing aggression and hyperactivity, treating obesity, improving reproduction efficiency, treating metabolic disorder, treating hypertension, treating hyperglycemia, treating insulin resistance, treating type 2 diabetes, and/or aiding in cancer and immune therapies In one embodiment, the glucocorticoid related disorder is stress related or results in stress.

High cortisol is known to result in weak, brittle and fragile bones and can shift calcium from the bones to the blood. Accordingly, in another embodiment, the present disclosure provides a method of maintaining or improving bone density comprising administering a composition of a preparation obtained from a plant of the family Marcgraviaceae and B) a preparation obtained from a plant of the family Platanaceae as disclosed herein or a preparation of Marcgraviaceae and/or Platanaceae to an animal in need thereof. Also provided herein is use of a composition of a preparation obtained from a plant of the family Marcgraviaceae and B) a preparation obtained from a plant of the family Platanaceae as disclosed herein or a preparation of Marcgraviaceae and/or Platanaceae for maintaining or improving bone density in an animal in need thereof. Further provided is use of a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for maintaining or improving bone density in an animal in need thereof. Even further provided is a composition of a preparation obtained from a plant of the family Marcgraviaceae and B) a preparation obtained from a plant of the family Platanaceae as disclosed herein or a preparation of Marcgraviaceae and/or Platanaceae for use in maintaining or improving bone density in an animal in need thereof.

High cortisol is also implicated in suppressing the immune system. Thus, in an embodiment, reduction of cortisol is useful for maintaining or improving an active immune system. Accordingly, also provided herein is a method of maintaining or improving an active immune system comprising administering a composition of a preparation obtained from a plant of the family Marcgraviaceae and B) a preparation obtained from a plant of the family Platanaceae as disclosed herein or a preparation of Marcgraviaceae and/or Platanaceae to an animal in need thereof. Also provided herein is use of a composition of a preparation obtained from a plant of the family Marcgraviaceae and B) a preparation obtained from a plant of the family Platanaceae as disclosed herein or a preparation of Marcgraviaceae and/or Platanaceae for maintaining or improving an active immune system in an animal in need thereof. Further provided is use of a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for maintaining or improving an active immune system in an animal in need thereof. Even further provided is a composition of a preparation obtained from a plant of the family Marcgraviaceae and B) a preparation obtained from a plant of the family Platanaceae as disclosed herein or a preparation of Marcgraviaceae and/or Platanaceae for use in maintaining or improving an active immune system in an animal in need thereof.

Cushing's syndrome is caused by overactive adrenal glands which stimulates the production of high levels of cortisol under the influence of increased production of ACTH. Thus, in another embodiment, methods and uses of reducing cortisol and/or ACTH are useful for treating Cushing's syndrome. Accordingly, also provided herein is a method of treating Cushing's syndrome comprising administering a composition of a preparation obtained from a plant of the family Marcgraviaceae and B) a preparation obtained from a plant of the family Platanaceae as disclosed herein or a preparation of Marcgraviaceae and/or Platanaceae to an animal in need thereof. Also provided herein is use of a composition of a preparation obtained from a plant of the family Marcgraviaceae and B) a preparation obtained from a plant of the family Platanaceae as disclosed herein or a preparation of Marcgraviaceae and/or Platanaceae for treating Cushing's syndrome in an animal in need thereof. Further provided is use of a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for treating Cushing's syndrome in an animal in need thereof. Even further provided is a composition of a preparation obtained from a plant of the family Marcgraviaceae and B) a preparation obtained from a plant of the family Platanaceae as disclosed herein or a preparation of Marcgraviaceae and/or Platanaceae for use in treating Cushing's syndrome in an animal in need thereof.

In yet another embodiment, there is provided a method of treating a disorder related to elevated levels of ACTH comprising administering a composition of a preparation obtained from a plant of the family Marcgraviaceae and B) a preparation obtained from a plant of the family Platanaceae as disclosed herein or a preparation of Marcgraviaceae and/or Platanaceae to an animal in need thereof. Also provided herein is use of a composition of a preparation obtained from a plant of the family Marcgraviaceae and B) a preparation obtained from a plant of the family Platanaceae as disclosed herein or a preparation of Marcgraviaceae and/or Platanaceae for treating a disorder related to elevated levels of ACTH in an animal in need thereof. Further provided is use of a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for treating a disorder related to elevated levels of ACTH in an animal in need thereof. Even further provided is a composition of a preparation obtained from a plant of the family Marcgraviaceae and B) a preparation obtained from a plant of the family Platanaceae as disclosed herein or a preparation of Marcgraviaceae and/or Platanaceae for use in treating a disorder related to elevated levels of ACTH in an animal in need thereof. In an embodiment, the disorder related to elevated levels of ACTH is Addison's Disease, Cushing's Syndrome or Adrenal Insufficiency.

High cortisol levels are associated with metabolic syndrome and the deposition of fat in the stomach area for storage (visceral obesity). High cortisol levels also increase motivation (via brain reward mechanisms) to consume calorie-dense (high sugar/high fat content) foods (Dallman, M. F. 2009). Thus, in yet another embodiment, reduction of cortisol is useful as an aid to weight loss. Accordingly, also provided herein is a method of treating obesity or reducing fat comprising administering a composition of a preparation obtained from a plant of the family Marcgraviaceae and B) a preparation obtained from a plant of the family Platanaceae as disclosed herein or a preparation of Marcgraviaceae and/or Platanaceae to an animal in need thereof. Also provided herein is use of a composition of a preparation obtained from a plant of the family Marcgraviaceae and B) a preparation obtained from a plant of the family Platanaceae as disclosed herein or a preparation of Marcgraviaceae and/or Platanaceae for treating obesity or reducing fat in an animal in need thereof. Further provided is use of a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for treating obesity or reducing fat in an animal in need thereof. Even further provided is a composition of a preparation obtained from a plant of the family Marcgraviaceae and B) a preparation obtained from a plant of the family Platanaceae as disclosed herein or a preparation of Marcgraviaceae and/or Platanaceae for use in treating obesity or reducing fat in an animal in need thereof.

High cortisol levels have been shown to result in suppression of the manufacturing of DHEA, which is the precursor of reproductive hormones, including estrogen, progesterone and testosterone. Animals under stress have a more difficult time becoming pregnant and methods for reducing cortisol would be useful to aid in reproductive efficiency. Accordingly, in a further embodiment, also provided herein is a method of improving reproductive efficiency comprising administering a composition of a preparation obtained from a plant of the family Marcgraviaceae and B) a preparation obtained from a plant of the family Platanaceae as disclosed herein or a preparation of Marcgraviaceae and/or Platanaceae to an animal in need thereof. Also provided herein is use of a composition of a preparation obtained from a plant of the family Marcgraviaceae and B) a preparation obtained from a plant of the family Platanaceae as disclosed herein or a preparation of Marcgraviaceae and/or Platanaceae for improving reproductive efficiency in an animal in need thereof. Further provided is use of a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for improving reproductive efficiency in an animal in need thereof. Even further provided is a composition of a preparation obtained from a plant of the family Marcgraviaceae and B) a preparation obtained from a plant of the family Platanaceae as disclosed herein or a preparation of Marcgraviaceae and/or Platanaceae for use in improving reproductive efficiency in an animal in need thereof. The term "improving reproductive efficiency" as used herein refers to increasing the likelihood of conceiving or maintaining a pregnancy compared to an untreated control.

High cortisol and low DHEA levels are also implicated in metabolic disorders, including, without limitation, Crohn's Disease and Ulcerative Colitis. Reduction of cortisol is useful for treating such metabolic disorders by lowering cortisol, increasing DHEA and reducing inflammation. Accordingly, in yet a further embodiment, also provided herein is a method of treating a metabolic disorder comprising administering a composition of a preparation obtained from a plant of the family Marcgraviaceae and B) a preparation obtained from a plant of the family Platanaceae as disclosed herein or a preparation of Marcgraviaceae and/or Platanaceae to an animal in need thereof. Also provided herein is use of a composition of a preparation obtained from a plant of the family Marcgraviaceae and B) a preparation obtained from a plant of the family Platanaceae as disclosed herein or a preparation of Marcgraviaceae and/or Platanaceae for treating a metabolic disorder in an animal in need thereof. Further provided is use of a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for treating a metabolic disorder in an animal in need thereof. Even further provided is a composition of a preparation obtained from a plant of the family Marcgraviaceae and B) a preparation obtained from a plant of the family Platanaceae as disclosed herein or a preparation of Marcgraviaceae and/or Platanaceae for use in treating a metabolic disorder in an animal in need thereof.

Cortisol levels are further implicated in hypertension and thus, in another embodiment, methods and uses for reducing cortisol are useful in treating hypertension. Accordingly, also provided herein is a method of treating hypertension comprising administering a composition of a preparation obtained from a plant of the family Marcgraviaceae and B) a preparation obtained from a plant of the family Platanaceae as disclosed herein or a preparation of Marcgraviaceae and/or Platanaceae to an animal in need thereof. Also provided herein is use of a composition of a preparation obtained from a plant of the family Marcgraviaceae and B) a preparation obtained from a plant of the family Platanaceae as disclosed herein or a preparation of Marcgraviaceae and/or Platanaceae for treating hypertension in an animal in need thereof. Further provided is use of a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for treating hypertension in an animal in need thereof. Even further is a composition of a preparation obtained from a plant of the family Marcgraviaceae and B) a preparation obtained from a plant of the family Platanaceae as disclosed herein or a preparation of Marcgraviaceae and/or Platanaceae for use in treating hypertension in an animal in need thereof.

Reduction of cortisol is useful in reducing high blood sugar, including, without limitation, for treating hyperglycemia, insulin resistance and Type 2 diabetes. Accordingly, in yet another embodiment, also provided herein is a method of reducing high blood sugar comprising administering a composition of a preparation obtained from a plant of the family Marcgraviaceae and B) a preparation obtained from a plant of the family Platanaceae as disclosed herein or a preparation of Marcgraviaceae and/or Platanaceae to an animal in need thereof. Also provided herein is use of a composition of a preparation obtained from a plant of the family Marcgraviaceae and B) a preparation obtained from a plant of the family Platanaceae as disclosed herein or a preparation of Marcgraviaceae and/or Platanaceae for reducing high blood sugar in an animal in need thereof. Further provided is use of a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for reducing high blood sugar in an animal in need thereof. Even further is a composition of a preparation obtained from a plant of the family Marcgraviaceae and B) a preparation obtained from a plant of the family Platanaceae as disclosed herein or a preparation of Marcgraviaceae and/or Platanaceae for use in reducing high blood sugar in an animal in need thereof. The term "reducing high blood sugar" as used herein refers to lowering blood sugar into the normal range in an animal that suffers from high blood sugar, including, without limitation, an animal that has hyperglycemia, insulin resistance and/or Type 2 diabetes.

Reduction of weight is useful for ameliorating number of conditions related to but not limited to general health, obesity, metabolic syndrome diseases and diabetes. Accordingly, in yet another embodiment, also provided herein is a method of reducing weight comprising administering a composition of a preparation obtained from a plant of the family Marcgraviaceae and B) a preparation obtained from a plant of the family Platanaceae as disclosed herein or a preparation of Marcgraviaceae and/or Platanaceae to an animal in need thereof. Also provided herein is use of a composition of a preparation obtained from a plant of the family Marcgraviaceae and B) a preparation obtained from a plant of the family Platanaceae as disclosed herein or a preparation of Marcgraviaceae and/or Platanaceae for reducing weight in an animal in need thereof. Further provided is use of a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for reducing weight in an animal in need thereof. Even further is a composition of a preparation obtained from a plant of the family Marcgraviaceae and B) a preparation obtained from a plant of the family Platanaceae as disclosed herein or a preparation of Marcgraviaceae and/or Platanaceae for use in reducing weight in an animal in need thereof. The term "reducing weight" as used herein refers to lowering the weight of the animal into the normal range for said an animal.

The term "treatment or treating" as used herein means an approach for obtaining beneficial or desired results, including clinical results. Beneficial or desired results can include, but are not limited to, alleviation or amelioration of one or more symptoms or conditions, diminishment of extent of condition, anxiety and/or stress, stabilized (i.e. not worsening) state of the condition, anxiety, or stress and preventing the condition, anxiety or stress. Thus, treatment can be administered while symptoms are present or prophylactically in advance of anticipated development of symptoms in animals at heightened risk of developing symptoms, for example, in animals facing an event that previously triggered anxiety or is reasonably anticipated to trigger anxiety or in animals that suffer from or are at risk of a condition associated with high levels of cortisol. Anxiety for animals facing an event is also typically described as anticipated anxiety (in animals) if recognized by the owner or animal caregiver and is described as conditioned anxiety if recognized by the actual animal.

The term "animal" as used herein refers to all members of the animal kingdom, including without limitation, humans, horse (equine), pig (susidae), sheep, goat, farmed fish (e.g. salmonids, catfish etc.) or crustacean (e.g. shrimp, prawns), bird (e.g. turkeys, fowls, chickens), cattle, endangered or captive species (e.g. zoo animal or aquarium animal), pet animal (e.g. dog (canine), cat (feline)). In one embodiment, the animal is a human.

The compositions or preparations disclosed herein may be administered or used in the methods disclosed herein in any manner, including without limitation, intranasally, intraocularly, sublingually, parenterally, intravenously, topically, intraperitoneally, orally, rectally, in food additive and feed rations.

The compositions or preparations disclosed herein may be used alone or in combination with other known agents useful for treating or preventing anxiety, and glucocorticoid-related conditions.

When used in combination with other agents, the compositions disclosed herein are suitably administered contemporaneously with those agents. As used herein, "contemporaneous administration" of two substances to an individual means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regiments is routine for one skilled in the art. In particular embodiments, two substances will be administered substantially simultaneously, i.e., within minutes of each other, or in a single composition that contains both substances.

The reduction of cortisol is also known to make cancer and immune therapies work more effectively. Accordingly, in another embodiment, there is provided a method of treating cancer or an immune condition comprising administering a cancer or immune therapeutic contemporaneously with a composition of a preparation obtained from a plant of the family Marcgraviaceae and B) a preparation obtained from a plant of the family Platanaceae as disclosed herein or a preparation of Marcgraviaceae and/or Platanaceae. Also provided herein is use of a cancer or immune therapeutic and a composition of a preparation obtained from a plant of the family Marcgraviaceae and B) a preparation obtained from a plant of the family Platanaceae as disclosed herein or a preparation of Marcgraviaceae and/or Platanaceae for treating cancer or an immune condition in an animal in need thereof. Further provided is use of a cancer or immune therapeutic and a composition of a preparation obtained from a plant of the family Marcgraviaceae and B) a preparation obtained from a plant of the family Platanaceae as disclosed herein or a preparation of Marcgraviaceae and/or Platanaceae in the preparation of a medicament for treating cancer or an immune condition in an animal in need thereof. Even further is a cancer or immune therapeutic and a composition of a preparation obtained from a plant of the family Marcgraviaceae and B) a preparation obtained from a plant of the family Platanaceae as disclosed herein or a preparation of Marcgraviaceae and/or Platanaceae for use in treating cancer or an immune condition in an animal in need thereof.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1: Treatment of Anxiety in Rats

The following example demonstrates that the combination of the plant material from *Souroubea* species and *Platanus* species is superior in treating anxiety in rats, compared to either plant species by itself. The example also demonstrates that the combination has broad anxiolytic properties as the effects were evident across three different anxiety and fear provoking models.

The objective of this study was to assess the anxiolytic effectiveness of the representative species from *Souroubea* and *Platanus*, and the combination of the two plant species in three rat test models: (1) Elevated plus maze (EPM), (2) Social interaction test (SI), and (3) Conditioned Emotional Response (CER) (Carlson 2010, File 2004, File 1992, Pellows 1985).

Materials and Methods

The *Souroubea gilgii* plant vine samples (labeled SS for *Souroubea* sp.) were harvested from a farm in Sarapiqui, Costa Rica. The samples were chipped, dried and powdered. Samples were dried overnight in a commercial plant drier at 35° C. and ground to 1 mm mesh.

The *Platanus occidentalis* tree bark (labeled PT for *Platanus* sp.) was collected in southern Ontario, Canada, dried, and ground to a 1 mm mesh powder. The particular tree was located in Ottawa Canada at the Central Experimental Farm (OCEF) and is referred to in collection documents and voucher specimens as PTB-OCEF and is known to be *Platanus occidentalis*.

The botanical plant materials tested were: (1) 1000 mg/kg *Souroubea gilgii* (SS), (2) 100 mg/kg *Platanus occidentalis* (PT), (3) 250 mg/kg of the combination of *Souroubea gilgii* and *Platanus occidentalis*, in a ratio of SS 55% to PT 45%, (SSPT), and (4) Control Vehicle (50% sweetened condensed milk as the carrier).

The behavioral experiments were conducted with male Sprague-Dawley rats (225-250 g body mass; Charles River Laboratories Inc., St. Constant, Quebec). Rats were housed individually and maintained under standard animal room conditions (clear Plexiglas cages, 24×30×18 cm, 12 h light-dark cycle, 21±1° C., 60% humidity, Purina® Lab Chow® and tap water ad libitum). All experimental procedures were approved by the Research Ethics Committee of the University of Ottawa and met the guidelines set out by the Canadian Council on Animal Care (CCAC). Rats (n=32) were handled for 7 days prior to the experiment to acclimatize to the experimenter and were orally administered a 50% solution of Eagle Brand sweetened condensed milk each day to familiarize them with the feeding procedure. All attempts were made to minimize the number of animals used in the study, while maintaining the integrity of the experiments and results.

The plant materials were all suspended in 50% sweetened condensed milk 1 to 4 days prior to testing and stored at 4° C. All rats were orally administered the respective treatments for three consecutive days (2 days and 60 minutes prior to testing). The dose per rat administered was at volume per weight ratio of 7.5 ml/kg with the SS, PT, SSPT and negative control vehicle. The dose was chosen based on the betulinic acid marker content in plant material to be equivalent to 1 mg/kg of animal body weight.

Behaviour: Elevated Plus Maze (EPM)

The EPM is a validated test used to assess anxiety-like behaviour in laboratory rodents (Pellow 1986). The EPM consists of two open arms (50×10 cm), two perpendicular arms enclosed by 40 cm high walls, and is placed 50 cm above the ground. The EPM is based on the conflict between the animal's instinct to explore its environment and its fear of exposed areas and heights. Black curtains surrounded the chamber to limit the influence of spatial cues and other extraneous stimuli. A video camera was mounted above the arena to permit remote monitoring and recording. Rats (n=8/group) were individually placed in the testing room for 1 hour acclimatization. Each rat was then placed onto the open central platform of the EPM (facing a closed arm). The rats behaviour was monitored for 5 minutes and scored as follows: (1) frequency of entries onto the open arms, (2) percentage of time spent on the open arms (time open/300× 100), (3) frequency of entries in the closed arms, and (4) unprotected head dips (UH); head protruding over the edge of an open arm and down toward the floor, which is an index of risk assessment behaviour. Between tests, the EPM was cleaned with 70% isopropanol. The percent of time in the open arms, frequency of open arm entries, and unprotected head dips are all validated measures of anxiety-like behaviour in the EPM. Increases in these measures are indicative of reduced anxiety, whereas decreases compared to vehicles suggest increased anxiety (File, 1992). In contrast, the frequency of closed arm entries is an index of general activity (Cruz, Frei, & Graeff, 1994).

Social Interaction (SI)

SI experiments were done under semi-aversive (high illumination, familiar environment) conditions. SI was assessed in a square gray Perspex arena (60×60 cm; 30 cm-high walls, divided into 5×5 squares each measuring 12 cm), illuminated by a bright light source (300 lux) located directly above the arena. A camera linked to a video recorder in an adjacent room was located directly above the arenas to permit remote monitoring/scoring and recording of the test sessions. The SI study had a total duration of three days. Rats were randomly assigned to either control or botanical treatment groups. Vehicle and botanical treated rats were orally administered their respective solutions daily across three days (at 10:00 a.m. for two days preceding testing, and then 60 min prior to being placed on the SI arena on the test day). The first and second day was used for habituation. On habituation day 1, rats along with their test day partner were placed in the arena for five minutes. On habituation day 2, rats were individually placed in the arena for a period of 5 min. On test day (third day), each rat was allocated to a partner based on body weight, such that members of a pair did not differ by >10 g. On test day (day 3), both rats of each pair were given either sweetened condensed milk vehicle or their respective treatments (n=8); 60 min prior to being placed into the arena for a 7 minute period. Time spent engaged in active social interaction (including sniffing, climbing over each other, following, allogrooming, play-fighting, anogenital sniffing, and grooming) was recorded by an observer blind to drug treatment. Locomotor activity in the arena was assessed by counting the number of squares crossed by the rat. Testing was performed between 10:00 A.M. and 2:00 P.M. in a randomized order. The arena was cleaned with 70% ethanol between each trial.

Conditioned Emotional Response (CER)

Apparatus: The conditioning chamber (Coulbourn Instruments) measured 31 cm×25 cm×30 cm. The front and back walls were made of clear Plexiglas and two side walls made of stainless steel panels. The floor was composed of 16 stainless steel rods (4 mm diameter, 1.4 cm apart), which were connected to a Coulbourn Instruments shock generator (model H13-16) that delivered constant current.

Procedure: Rats (n=8/group) completed 1 day of training followed by a day of testing 24-h later. During the contextual training phase, subjects were laced in the conditioning chamber where they received 6 footshocks (1.0 mA; 1-s in duration) with an average intertrial interval (ITI) of 1-min. On the test days, contextual fear was assessed over a 15-min period by placing them in the conditioning chamber where they had previously been shocked. Freezing behavior was determined by the absence of movement excluding involuntary respiratory. The absence or presence of complete immobility was recorded over the course of the test period. Evaluations of freezing were conducted by trained experimenters blind to the drug condition. Between each training and testing session, cages were cleaned with 70% ethanol.

Data Analysis

Data obtained from the EPM, SI and CER tests were analyzed using one-way analysis of variance (ANOVA) for each of the behavioral measures with treatment condition as the between-group factor. Follow-up analyses were conducted using t tests with a Bonferroni correction to protect the α at 0.05.

Results

Elevated Plus Maze (EPM)

The results in FIGS. 1 (A and B) shows that only the combination SSPT treated animals had a significant increase in the percentage of time spent in the open arms 2.871=p<0.01) and an increase in the number of unpredicted head dips 3.293=p<0.01).

Social Interaction Test (SI)

Figure 2:
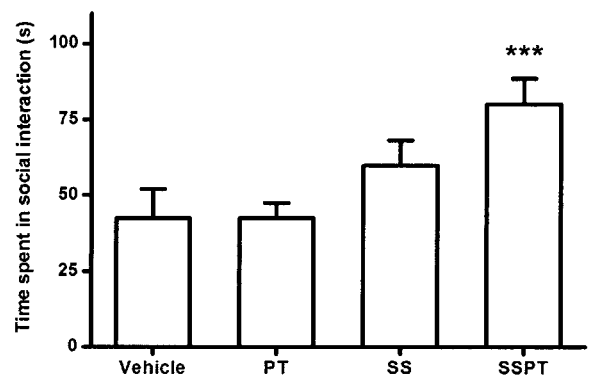
FIG. 2 shows the time that the rats spent in social interaction following three consecutive daily administrations of respective treatments (SS, PT, SSPT and vehicle). *** $p<0.001$ indicates a significant difference from vehicle.

In the SI experiment (FIG. 2), oral administration of the combination SSPT elicited a significant increase in the amount of time spent engaged in active social interaction compared to vehicle treated rats; p<0.001. The SI experiment also indicated no increase or decrease of locomotor activity in any of the groups compared to vehicles.

Conditioned Emotional Response (CER)

Figure 3:
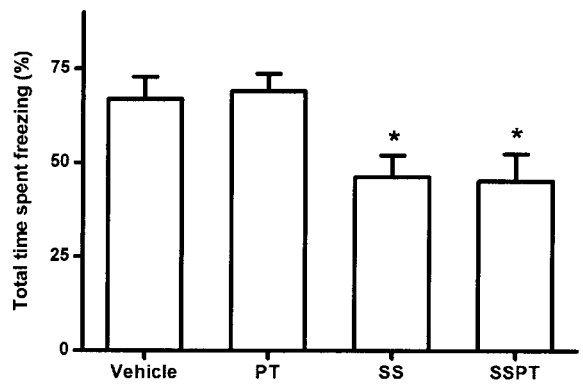
FIG. 3 shows percentage of total time that rats engaged in freezing following three consecutive daily administrations of respective treatments (SS, PT, SSPT and vehicle) in the contextual conditioned emotion response (CER) paradigm. * $p<0.05$, indicate significant differences from vehicle.
Figure 4:
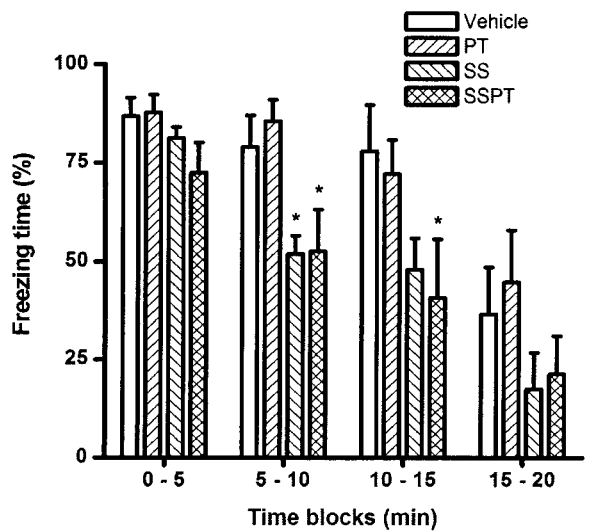
FIG. 4 shows the breakdown in 4 time blocks of the freezing time for rats expressed as absolute values following three consecutive daily oral administrations of respective treatments (SS, PT, SSPT and vehicle) in the contextual CER paradigm. * $p<0.05$, indicate significant differences from vehicle.

In the contextual CER test, total time spent freezing was significantly lower in the combination SSPT treated rats compared to those that received the vehicle treatment, p<0.05; (FIG. 3). Follow-up analyses revealed that the reduction in time spent freezing in SSPT treated rats compared to vehicle treated rats was observed only in the second and third time blocks (FIG. 4). The SS treated rats showed a significant decrease in time spent freezing compared to vehicle treated rats during only the second time block. Self-grooming behavior was also monitored but showed no significant differences across treatment groups.

Discussion

The results of this study demonstrate that the combination SSPT alleviated both anxiety and fear responses in the rat. Through standard behavioral models, the measures of both unconditioned anxiety responses (EPM, SI) and learned fear responses (CER) indicated a reduction in anxiety compared to control animals. In the EPM, administration of the SSPT combination increased time spent on the open arms and increased the number of unprotected head dips which are indicative of an anti-anxiety effect (Pellow 1985). Similarly in the SI test, administration of the combination increased time spent engaged in active social interaction which is a behavioral effect also consistent with a reduction in anxiety levels (reference). It is important to note that increased social interaction and increased time spent on the open arms of the EPM was not accompanied by changes in locomotor activity. Indeed, no sedation in overall motor activity was observed in both the EPM and SI behavioral paradigms, which is a side effect of conventional drugs like diazepam.

The effects of the combination SSPT were also tested in a CER test which is a model of learned fear (Carlson 2010). Administration of both the SS material and the combination decreased the CER (freezing response) compared to vehicle treated rats.

Taken together, these findings demonstrate that the combination SSPT has widespread anxiolytic properties as the effects were evident across a variety of different anxiety and fear provoking situations.

These plants, and combinations thereof, could also have potential applications in the veterinary sector. They could help alleviate certain anxiogenic factors that are presently influencing the livestock in this industry. Animals raised in large scale industrial farms are housed in an environmentally stressful context and express high levels of glucocorticoids, resulting in reduced reproductive efficiency and limited yield in overall productivity. Combining anxiolytic plant material with feed might be a viable solution in reducing circulating glucocorticoids in farm animals.

Example 2: Reduction in Anxiety, Stress and Glucocorticoid Levels in Dogs

This example demonstrates that the elevated levels of the glucocorticoid, cortisol, in dogs, which is increased in response to stress, can be reduced with the use of a combination of plant materials from a *Souroubea* sp. (SS) and a *Platanus* sp. (PT).

The objective of this study was to: (1) assess the anxiolytic activity and (2) stress reduction in dogs treated with different doses of a combination of *Souroubea* sp. and *Platanus* sp. (SSPT) plant materials. The composition of the test material was SS:PT: 55:45 (% by weight), which was incorporated into a tablet that was of 50% by weight of SSPT.

The experiment was designed to compare the effectiveness of SSPT at four dose levels and compare these to a placebo control. Three different types of anxiety models were examined: a physiological anxiety model, an observational anxiety model and a model based on measurements of behavioral activity. A noise-induced anxiety model (DePorter, T. et al., 2012) was used as a stressor in which canine subjects were placed in an open-field test room and after three minutes were exposed to the taped sound of intermittent thunder over a three minute period. There was also a three minute post-thunder interval. All subjects received two thunder tests, one at baseline and one under the treatment condition. Subjects also received two additional open field tests in which thunder was not introduced.

A total of 50 dogs participated in the study. Subjects were placed into five equivalent groups of 10 animals per group based on a combination of observed anxiety in response to the thunder, and change in blood cortisol level at 10 minutes following exposure to thunder.

The five groups included a placebo control and four treatment groups that were administered SSPT at doses designated as ×0.5, ×1, ×2 and ×4. SS contains approximately 0.1% betulinic acid on a dry matter basis, and this was used as the marker compound to decide the dose levels for each test group. The dose levels tested were equivalent to 0.5, 1.0, 2.0 and 4.0 mg of betulinic acid/kg body weight respectively.

There were four variables measured: blood cortisol, heart rate, observed anxiety (using an observational anxiety scale) and objective measures of behavioral activity.

Results & Discussion

Figure 5:
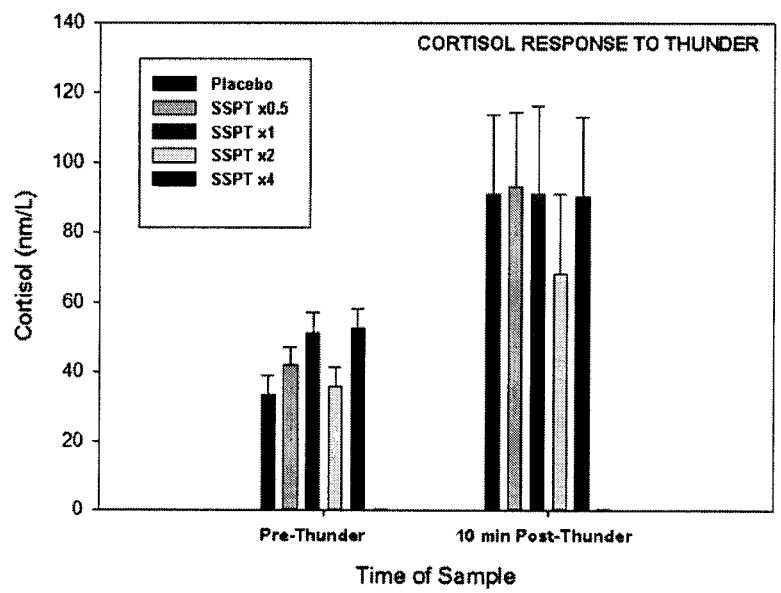
FIG. 5 shows that all treatment groups prior to any drug administration, responded to the thunder stressor by having an elevated level of cortisol, thus validating the protocol. This was prior to any treatment dose of the combination of *Souroubea* and *Platanus* species (SSPT). The y-axis shows percent change in serum cortisol at 10 min post thunder when compared to baseline. The x-axis shows all the treatment groups SSPT at 0 (placebo) and ×0.5, ×1, ×2 and ×4 times SSPT dose.
Figure 6:
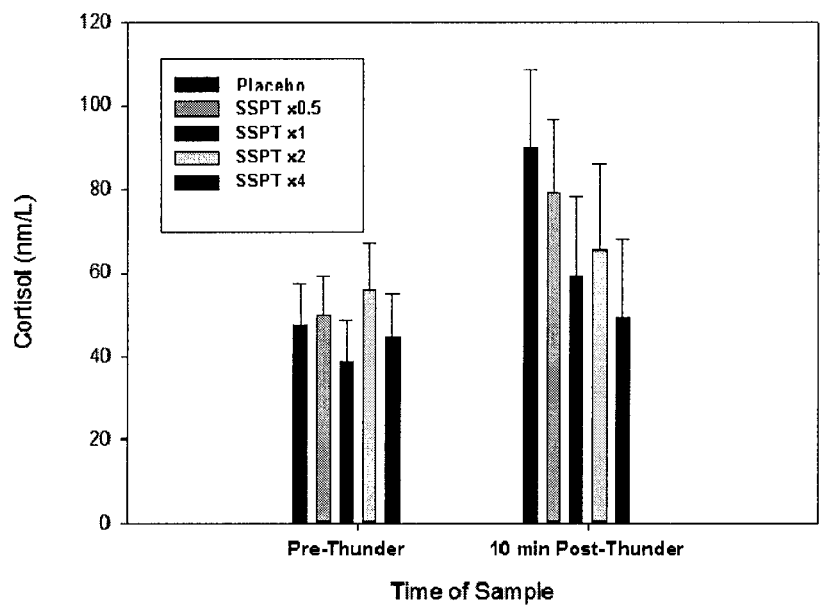
FIG. 6 shows the response to thunder in responder dogs and that there is a dose dependent reduction in cortisol levels in SSPT treated dogs.

The baseline cortisol results (FIG. 5) demonstrated increased blood cortisol in response to the thunder in all test groups. In contrast the results during the product (FIG. 6) showed an overall reduction in thunder-induced cortisol increases when compared to baseline in all treatment groups. In addition, the response of the groups administered SSPT varied as a function of dose; the greater the dose, the smaller the cortisol response. It was further noted that the cortisol response varied between individual subjects, with some dogs being classified as responders and others as non-responders. Non-responders are dogs that are not affected by the stress of thunder and thus would not have an increase in cortisol. When only responder dogs were evaluated, a statistically significant response (p<0.05) was demonstrated in the reduction of cortisol elevation in response to the thunder-induced stress in animals treated with SSPT and that the reduction response was dose dependent as seen in FIG. 6.

When examining cortisol in the placebo group, animals returning to the test room developed higher cortisol levels in the pre-thunder phase of testing, a response consistent with a conditioned anxiety response. In all SSPT treatment groups, the cortisol-increase response was reduced in all but the lowest dose group (×0.5).

The heart rate measure did not show a differential response to the thunderstorm during either baseline or treatment phase. The absence of a significant increase in heart rate probably reflects the fact that heart rate was not taken immediately after presentation of thunder.

There were three observational measures of anxiety. The first was a measure of autonomic anxiety, which was manifested by activities associated with behavioral inactivity or withdrawal (comparable to the freezing parameter in the rat studies in Example 1). The second was a measure of active anxiety, which was associated with increased arousal and nervous activity. The third, a measure of global anxiety, was a composite that took into consideration both autonomic and active anxiety. All three measures increased significantly during the thunder and post-thunder intervals. In addition, when subjects were tested following a thunder session, their anxiety scores were increased at the beginning of the next session, which represents a conditioned anxiety. Under the test condition, the global anxiety scores in the SSPT treatment groups were significantly reduced compared to baseline.

During the treatment phase, the locomotor activity measure varied as a function of group, with all SSPT treatment groups showing little change in activity while the Control group showed a decrease in locomotion.

Figure 7:
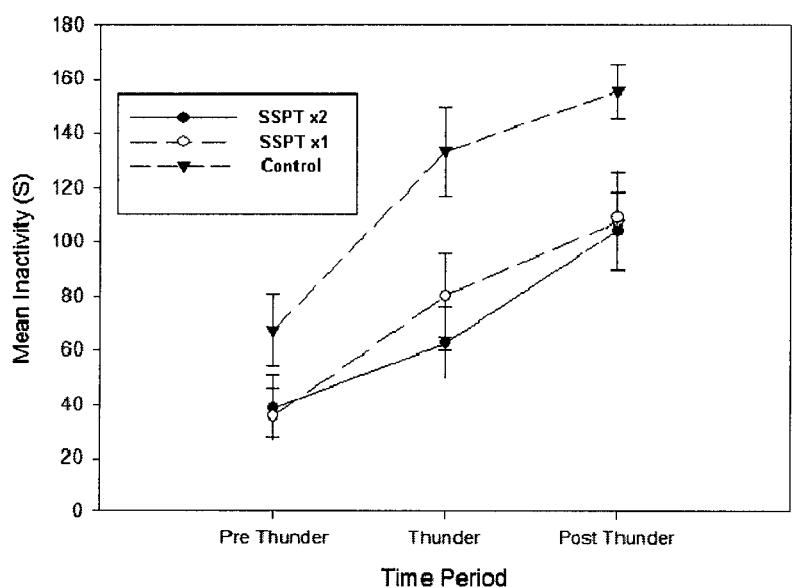
FIG. 7 shows a significant group effect for inactivity measures. This was a result of the Control group differing significantly from the SSPTx1 and SSPTx2 treated dogs.

Behavioral inactivity also varied as a function of group. FIG. 7 shows that SSPT treatment groups×2 and ×1 differed significantly ($p<0.05$) from the control group, in showing less overall inactivity.

Figure 8:
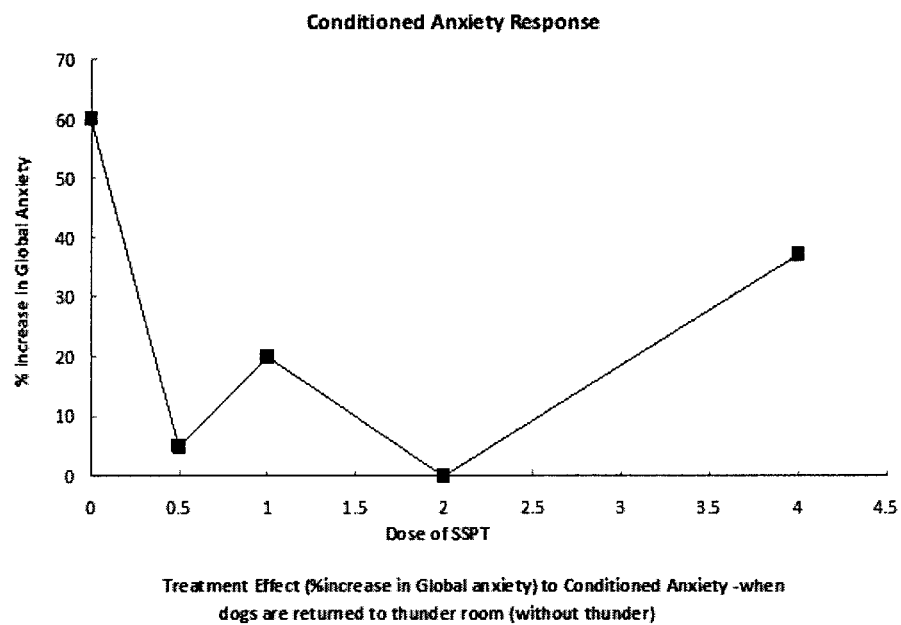
FIG. 8 shows the percent increase in Conditioned Global Anxiety in relation to the SSPT treatment dose and the percentage increase in Global Anxiety when dogs are returned to the thunder room with no thunder stimulation. ×1 treatment dose=1 mg/kg of betulinic acid.

Conditioned anxiety involved comparing the animal's observed performance (negative or positive anxiety) during the first three minutes (post-thunder) of every test. The results (FIG. 8) demonstrated that the control group showed a conditioned thunder response. However, the SSPT-treated groups did not show this conditioned response. This suggests that SSPT could be effective in reducing the development of conditioned anxiety responses.

Health and palatability of the test compound was also monitored over the course of the trial. There were no issues with the palatability of the SSPT tablets used in dosing. To the contrary, the formulation used was judged to be highly palatable. Also, there was no evidence that SSPT produced any adverse effects in any animals.

These findings support the use of SSPT in reducing stress and anxiety in dogs. This example demonstrates the effectiveness of the combination of plant materials combination of *Souroubea* sp. and *Platanus* sp. in reducing noise-induced stress, as measured by a decrease in cortisol release and an increase in activity and reduction of inactivity in response to thunder. The results also suggest that SSPT may be effective in reducing conditioned anxiety. These results also demonstrate that an increase in cortisol, due to stress, can be reduced, suggesting that SSPT should be useful for reducing increased glucocorticoids caused by factors other than stress.

Furthermore, dog studies are an acceptable model for testing anxiety and stress, and the results are applicable to other animals and humans.

Example 3: Cortisol Lowering in Fish

A Botanical Extract of *Souroubea* species (SS) has Cortisol Lowering Capacity in Stressed Fish This example demonstrates that *S. sympetala* extracts act at the site of cortisol synthesis (inter-renal cells in Rainbow trout) to lower cortisol response to an ACTH challenge in vitro.

The objective of this experiment was an in vitro and in vivo assessment in rainbow trout to examine the cortisol-reducing activity of *S. sympetala* extracts.

Materials and Methods

Chemicals: Analytical grade HPLC solvents were purchased from J. T. Baker (USA). Betulinic acid (BA) was obtained from Sigma-Aldrich (St. Louis, Mo.). Extraction grade solvent (ethyl acetate) was purchased from Fisher Scientific (Ottawa, ON Canada).

Plant material: Fresh samples of wild *S. sympetala* were collected under permit in Tortuguero, Costa Rica. Samples were dried overnight in a commercial plant drier at 35° C. and ground to 2 mm mesh.

Conventional solvent extraction: Samples (2 g) were incubated, with shaking, in 40 mL (1:20 weight: volume) ethyl acetate (EtOAc) for 12-15 h at room temperature (RT). The solvent was filtered (Whatman #1) and the filter cake re-extracted twice as above, with half as much EtOAc (1:10 and 1:5). The total solvent from the three extractions was combined for an exhaustive extraction. The solvent was removed by rotary evaporation with a Yamato Rotary Evaporator RE50 (Yamato Scientific, Japan) at 40° C., lyophilized (Super Modulyo, Thermo Electron, USA) and stored in opaque glass vials at 4° C. Total BA content of extracts was determined as previously described (Mullally et al., 2008).

Animals: Female juvenile rainbow trout (*Oncorhynchus mykiss*), 75-150 g, were obtained from Linwood Acres Trout Farm (Campellcroft, ON, Canada). Fish were transported to the University of Ottawa Aquatic Care Facility and maintained in fiberglass holding tanks (110-115 L) continuously supplied with aerated, dechloraminated City of Ottawa tap water at 13° C. Fish were subjected to a constant 12 L:12 D photoperiod and fed five times per week with commercial trout pellets (Classic Floating Trout Grower, Martin Mills, Tavistock, ON). All experiments were carried out under protocols approved by the University of Ottawa Protocol Review Committee and adhere to published guidelines of the Canadian Council on Animal Care for the use of animals in teaching and research.

Preparation of Cell Suspensions: Trout head kidney cells were prepared as adapted from Leblond et al., 2001. Briefly, fish were anesthetized with benzocaine (30 to 35 mg/L), blood was collected by caudal puncture into heparinized syringes and fish were then euthanized by a sharp blow to the head followed by trans-spinal sectioning. The head kidney was removed and placed in a solution of enriched minimum essential media (eMEM, Sigma-Aldrich) supplemented with collagenase/dispase (2 mg/mL). The tissue was manually disrupted by gently pressing it on the interior walls of the tube with a small spatula and incubated for 1 h at 10-13° C. with shaking. The homogenate was then sequentially filtered (200 µm filter, rinsed with MEM, then a 75 µm filter and rinsed with MEM), centrifuged (260 g, 10-13° C., 5 min) and the pellet resuspended in 1 mL MEM.

Stimulation of Head Kidney Cells with *S. sympetala* Extract: Cells were plated in a 96-well microtiter plate with 150 µL containing $50 \times 10^6$ cells/well. Cells were incubated with *S. sympetala* extract (1, 3, 10, 30 or 100 µg/L) dissolved in DMSO (final concentration of DMSO: 0.3% v/v) for 60 min at 10-13° C., then stimulated with 1 U/ml ACTH (Sigma-Aldrich) and incubated for an additional 60 min. Then cells were collected and transferred to 1.5 mL conical plastic tubes and centrifuged (20,000×g, 2 min); the supernatant was collected and flash frozen in liquid nitrogen for subsequent cortisol assay using a commercially available, standard RIA (MP Biomedicals Ltd., Solon, ON). The assay was assessed for cytotoxicity at the end of the experiment with the lactate dehydrogenase (LDH) assay according to Mommsen and Moon (Mommsen and Moon, 1987). Four control wells were prepared: DMSO blank (0.3% v/v), DMSO plus ACTH (1 Units of activity (U)/mL), eMEM blank and eMEM plus ACTH (1 U/mL). Statistical Analyses: One-way and two-way analyses of variance (ANOVA) with Bonferonni studentized range tests were performed for mean comparisons (Zar, 1999). Kolmogorov-Schmirnoff and Levene's tests were used to verify the normality of distribution and the homogeneity of residual variance, respectively. In cases where the data did not meet assumptions of the parametric tests, they were transformed. All of the Fisher statistics (F), degrees of freedom (df), and p-value estimates were calculated with S-PLUS software version 7.0 (Insightful Corp., Seattle, Wash.). Data are reported as means±S.E.M and the level of significance was set at $p<0.05$. The effective concentration at which the cortisol response was reduced to 50% (EC50) was calculated for $S.$ $sympetala$ extract by determining the equation of the linear regressions for extract treatment in the head kidney assay.

Results

Incubation of Head Kidney Cells with $S.$ $Sympetala$ Extract

Figure 9:
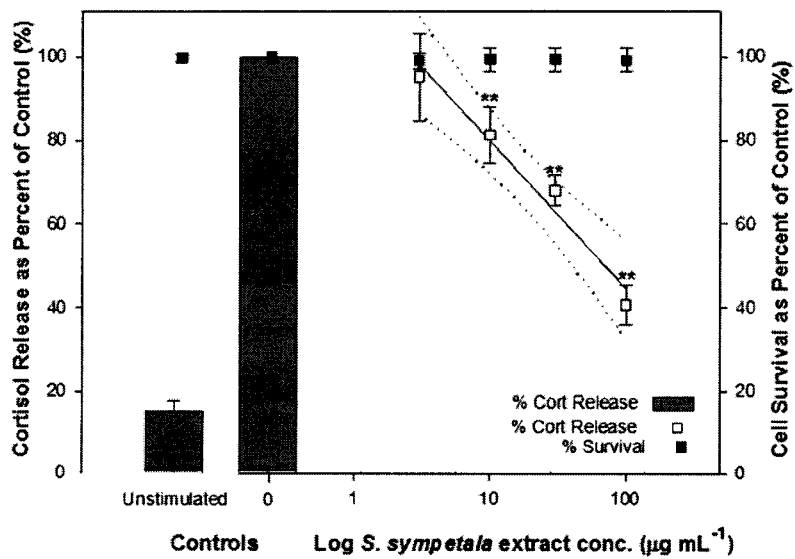
FIG. 9 shows the effect of incubation with *S. sympetala* extract on cortisol released from rainbow trout (*Oncorhynchus mykiss*) head kidney cells with and without challenge with 1 U/mL adrenocorticotropic hormone (ACTH). Open squares represent cortisol release as a percent of the positive control (0); closed squares represent cell viability at each concentration as a percent of positive control (0). Values represent the group mean±S.E.M of n=6; dotted line represents the 95% confidence intervals, linear regression equation: y=−22.45 (log extract concentration)+91.62, R2=0.60, $p<0.01$, EC50=71.45 µg/mL.** Indicates significant difference from positive control (0), $p<0.001$, one-way ANOVA, multiple comparisons of means, Bonferonni correction. Unstimulated: cells incubated with minimal essential media (MEM); 0: cells incubated with MEM+1 U/mLACTH.

Rainbow trout head kidney cells pre-incubated with $S.$ $sympetala$ extract (3, 10, 30 and 100 μg/mL) released less cortisol in response to an ACTH (1 U/mL) challenge than the positive control group (MEM+ACTH, no $S.$ $sympetala$ extract) (FIG. 9). A linear regression was fit to the log extract concentration, such that cortisol release=−22.45 (log extract concentration)+91.62, $r^2=0.6$, $p<0.01$. Incubation with $S.$ $sympetala$ extract had no significant effect on cell viability (as measured by LDH leakage) in the assay as compared to the negative (un-stimulated) or positive (0, MEM+ACTH) controls.

Discussion

This study examined the putative cortisol lowering capacity of $S.$ $sympetala$ extract using an in vitro head kidney assay and an in vivo net-restraint assay in rainbow trout, $Oncorhynchus$ $mykiss$. The observed effects revealed in both assays a cortisol lowering effect of $S.$ $sympetala$ plant extract. Because the cortisol lowering is observed in the head kidney cell stimulated with ACTH, it can be confirmed that a site of inhibition is the biosynthesis of cortisol in these cells.

These results suggest that the $S.$ $sympetala$ extracts could be used in standard aquaculture procedures shown to induce cortisol release in fish, such as overcrowding, transport, handling, grading and poor water quality (Barton, 2000; Ruyet et al., 2008; Schreck et al., 2001; Trenzado et al., 2008) and also useful in other aquaculture species.

Example 4: Cortisol Lowering in Pigs

The effect on production performance of feeding nursery piglets with a $Souroubea$ sp. plant supplement to lower cortisol and reduce stress related responses.

The test materials used in the study were the $Souroubea$ $gilgii$ and purified betulinic acid. The $Souroubea$ $gigli$ plant samples (labelled SS for $Souroubea$ sp.) were harvested from the canals in Tortuguero, Costa Rica. The samples were chipped, dried and powdered. Samples were dried overnight in a commercial plant drier at 35° C. and ground to 1 mm mesh.

The objective of the study was to investigate the production performance and stress related responses in nursery piglets that were fed a supplemented of either dried $Souroubea$ $gilgii$ plant material (SS) or one of its active anxiolytic compounds, purified betulinic acid (BA). The following parameters were evaluated: (1) plasma levels of Acute Phase Proteins (APP) and cortisol, (2) behavioral and stress related aggressive interactions and injuries (aggressive pushing, number of fights and the duration of fights in seconds), (3) production performance parameters (average daily gain (ADG), feed intake, feed efficiency (kg feed/kg body weight gain)) and (4) health evaluation (incidence of disease, disease treatments and deaths).

The study included 300 piglets that were 21 days of age at the start of the experiment (day of weaning and first day of treatment). The piglets were treated at days 0 and 21 and monitored over a 39 day period. The pigs were 60 days of age at the end of the study. Pigs were randomly assigned to one of five treatment groups, with 60 pigs in each group: (1) Group A. untreated control, (2) Group B. 0.5 mg BA/kg body weight, (3) Group C. 1 mg BA/kg body weight, (4) Group D. 2 mg BA/kg body weight and (5) Group E. SS group, 500 mg ground SS leaves/kg body weight (BA concentration equivalent to 0.5 mg BA/kg body weight).

Blood samples from 8 pigs in each treatment group were drawn on days 0, 2, 7, 14, 21 and 39 for a total of 240 blood samples, to determine plasma APP and cortisol levels. The same pigs from each treatment group were used for each blood sample day. Pigs were also weighed and feed intake was measured on these days to calculate performance parameters.

Results:

Plasma Samples

Figure 10:
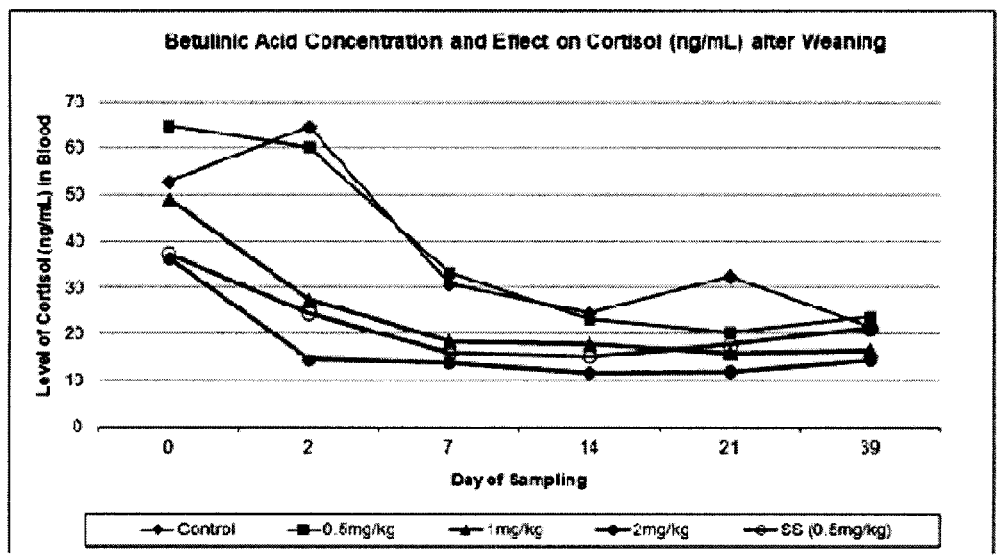
FIG. 10 shows the blood cortisol levels in pigs on various days after weaning and at different levels of betulinic acid and SS treatment. 1) Group A. untreated control, 2) Group B. 0.5 mg BA/kg body weight, 3) Group C. 1 mg BA/kg body weight, 4) Group D. 2 mg BA/kg body weight and 5) Group E. SS (marker BA concentration equivalent to BA 0.5 mg/kg.)

There was no significant difference in regards to plasma APP concentrations between any of the treatment groups at any of the sampling times. FIG. 10 shows that pigs in Groups C. (1 mg/kg BA), D. (2 mg/kg BA) and E. (500 mg/kg SS) had significantly lower plasma cortisol levels when compared to pigs in Groups A. and B. on day 2 ($p<0.01$). Pigs in Group D. had significantly lower plasma cortisol levels when compared to pigs in Group A. on days 7 and 14 ($p<0.05$). There was no significant difference in plasma cortisol concentration between any of the treatment groups after day 14.

Aggressive Behavior and Injuries

There were no significant differences between any of the groups with regards to the number of bites. Pigs in Group E. (SS group) demonstrated significantly less pushing behavior when compared to pigs in Group A. ($p<0.01$). There were no significant differences with regards to injuries between any of the groups.

Performance

There was no significant difference in average daily gain between any of the treatment groups at the end of the study (day 39 of the study). Pigs in Groups C. and D. had significantly less feed intake compared to Group A. (control group) between days 7 and 14 of the study. Pigs in Group D. had a significantly lower feed intake to weight gain ratio compared to Group A. between days 7 and 14. Pigs in Groups C. and D. had significantly lower body weights compared to the Group A. at day 14.

By day 21 of the study, there was no difference in body weights, feed intake, feed efficiency or average daily gain between any of the treatment groups. Although there did not appear to be any production benefit to the treatments in this study, there was also no detriment.

Health Evaluation

No major disease occurred during the study, and therefore no therapeutic antibiotic use was required.

Conclusions

The reduction in plasma cortisol levels during the first two days after weaning suggests that a $Souroubea$ sp. plant material and/or one or more of its active ingredients, besides betulinic acid, can decrease cortisol and stress in nursery pigs during the first few days after weaning. The dose required to achieve this effect was equivalent to 0.5 mg BA/kg when fed as the whole leaf *Souroubea* sp. (*S. gilgii*) plant material, and 1 mg BA/kg when a purified betulinic acid was fed alone. This indicates that there are other active components besides BA in the whole leaf botanical product. At a dose of 2 mg BA/kg, plasma cortisol levels were significantly reduced for the first 14 days post-weaning.

The first few days following weaning is a period of very high stress for piglets. Therefore, *Souroubea* spp. plant materials may be beneficial in reducing the stress associated with weaning by reducing circulating cortisol levels.

*Souroubea* sp. treated piglets were significantly less aggressive during the immediate post-weaning phase, as evidenced by a reduction in pushing behavior compared to pigs in the control group. Pigs in this treatment group (E.) also showed a lower severity of injuries on the ears and shoulders during the first few days after weaning. BA appeared to have little effect on the aggressive behavior and extent of injuries, except at the highest dose of 2 mg/kg (Group D.), where it appeared to reduce the number of wounds.

Example 5—Treatment of Cushing's Syndrome in Dogs

An older, 20 kg dog is presented to the veterinary clinic with a rough coat and hair loss (alopecia), polydipsia and polyuria, increased appetite with weight loss and a pot-bellied appearance. A tentative diagnosis of Cushing's disease is made and blood and urine samples are taken for testing. There is an increase in urine cortisol and the urine cortisol:creatinine ratio. The low-dose dexamethasone suppression test is positive and abdominal ultrasound does not indicate peritoneal cancer. Cushing's disease is confirmed. The animal is fed 2 grams per day of powdered SSPT plant material (SS to PT ratio is 55% SS and 45% PT) in tablet form. After one month, retesting indicates an improvement in all of the previous parameters. The animal will continue to be fed SSPT tablets on a maintenance regiment and blood and urine samples will be taken each 3 months.

Example 6—Treatment of Dyslipidemia and Weight Control in Mice

In this example the mice fed with high fat diet supplemented with SSPT show a decrease in cortisol concomitant with improvement in fatty acid profile. The effect of SSPT on cortisol levels, fatty acid levels and weight is examined using 10-week female C57BL/6 mice (Jackson Laboratory, Bar Harbor, Me., USA.) that are initially maintained on normal rodent diet and then fed on the atherogenic diet for 12 weeks as described in Li et al. (2008). Mice are divided into three groups that are fed a normal diet, or switched to a high fat diet or atherogenic diet. Mice in each group are further divided into two sub-groups, and each diet is either supplemented with or without 1 g/kg per day of powdered SSPT plant material (SS to PT ratio is 55% SS and 45% PT). Mice are weighed before the switch in diet and then at weeks, 4, 8 and 12. Blood samples are taken before the change in diet and then at weeks 4, 8 and 12. The plasma lipid levels, glucose and other parameters are measured as described in Li et al. (2008). Mice fed with diets supplemented with SSPT show an improvement in the fatty acid profile, lower hypercholesterolemia and a decrease in weight, in comparison with mice with non-supplemented diets.

Example 7—Alternative Ratios of SSPT in Lowering Cortisol Using Rats

The following example demonstrates that various combinations of the plant material from *Souroubea* species (SS) and *Platanus* species (PT) are effective in lowering cortisol in rats The example utilizes fear provoking models to help elevate cortisol. The objective of this study was to assess the cortisol lowering effectiveness of the SSPT combination(s) of the two plant species in the restraint rat test model.

Materials and Methods

The source and preparation of *Souroubea gilgii* plant vine samples (SS) and the *Platanus occidentalis* tree bark (PT) used in this experiment are described in Example 1.

The plant materials tested were: (1) *Souroubea gilgii* (SS), (2) *Platanus occidentalis* (PT), (3) the combination of SS and PT in a ratio of SS 25% to PT 75% ($SSPT_{2575}$), (4) SS and PT in a ratio of SS 75% to PT 25% ($SSPT_{7525}$), (5) SS and PT in a ratio of SS 85% to PT 15% ($SSPT_{8515}$) and (6) Control vehicle (50% sweetened condensed milk). The concentration of the solution for each ration and controls are outlined in Table 1.

TABLE 1

Concentration of dry botanical in suspension and volume delivered per mass of animal.

| Group name | Ratio of P. occidentalis | Ratio of S. sympetala | Concentration of Solution |
| --- | --- | --- | --- |
| Vehicle | 0% | 0% | 0 + 0 mg/kg |
| 100% PT | 100% | 0% | 100 + 0 mg/kg |
| 75% PT | 75% | 25% | 75 + 250 mg/kg |
| 25% PT | 25% | 75% | 25 + 750 mg/kg |
| 15% PT | 15% | 85% | 15 + 850 mg/kg |
| 100% SS | 0% | 100% | 0 + 1000 mg/kg |

The restraint experiments were conducted with male Sprague-Dawley rats (200 g-250 g body weight; Charles River Laboratories Inc., St. Constant, Quebec). The rats (n=8) were housed in pairs until after the completion to the first paradigm (approximately 10 days following arrival to the lab). They were housed individually for the remainder of the study. The rats were maintained under standard animal room conditions (clear Plexiglas cages, 24×30×18 cm, 12 h light-dark cycle, 21±1° C., 60% humidity, Purina Lab Chow and tap water ad libitum). Efforts were made to avoid any situation potentially stressful to the animals such as minimal handling and exposure to noise. All experimental procedures were approved by the Research Ethics Committee of the University of Ottawa and met the guidelines set out by the Canadian Council on Animal Care (CCAC). Prior to the administration of the plant materials, the rats were habituated to the taste of the drug vehicle; sweetened condensed milk. They were given Eagle Brand® sweetened condensed milk (diluted 50:50 with water) once a day for five consecutive days prior to the drug administration. Initially, all of the animals were wrapped in a blanket while the syringe containing the milk was inserted in to their cheek pocket. Since the taste of the milk was appealing, by the third administration, most of the animals freely consumed the milk from a syringe inserted between the bars of their cage.

Starting 2 days prior to the test, the plant extracts were suspended in the sweetened condensed milk solution. Enough solution was prepared for 3 administrations and was store at 2-8° C. between feedings. The volume of suspension administered was adjusted on Day 1 of each session. Each rat was weighed prior to their feeding and received a volume calculated from their weight using a 3 ml plastic syringe. All rats were orally administered the respective treatments (n=8) three times before testing—one dose on each of the 2 days preceding the test (between 9:00 and 11:00 am) and then the he $3^{rd}$ dose was administered on the test day, 1 hr prior to testing. The volume per mass ratio of all treatment groups was 7.5 ml/kg (Khan et al. 1999).

Rats were restrained by gently inserting them in a Rodent Restraint Cone (Harvard Apparatus, Mass.). Rats were restrained for 2 minutes (Khan et al. 1999). The first blood sample (baseline) was collected using the venepuncture method immediately after the onset of restraint.

Rats were placed on a table, and their tails were cleaned with gauze soaked in sterile water. Whole blood samples were obtained through venepuncture by prickling the end of the tail using a 30 G needle. Two drops of blood (approximately 15-25 [micro]l from each animal) were collected on Schleicher and Schuell specimen collection paper (Whatman International Ltd., Maidstone, UK). Blood was collected to completely soak through the collection paper and form a circular spot with a diameter larger than 3.0 mm. The drop paper samples were dried overnight at room temperature and then stored at −4° C.

Quantification of corticosterone from drop samples were carried out by the method described in Milot et al. (2012). A 3.0-mm-diameter circle was punched from the collection paper containing each drop sample, using a Gem Hole Punch (McGill Inc., Marengo, Ill.), and placed in a tube containing 200 μl of Dulbecco's phosphate-buffered saline (DPBS; Sigma-Aldrich, St. Louis, Mo.) containing 0.1% gelatin (Avantor Performance Materials, Phillipsburg, N.J.). The tubes were shaken in an orbital shaker at 90 r.p.m. for h at 24° C. and then refrigerated for 48 h at 4° C. before the radioimmunoassay procedure. Corticosterone was quantified using a commercially available radioimmunoassay kit (Corticosterone Double Antibody 125l RIA Kit; MP Biomedicals, Solon, Ohio). The manufacturer's protocol to prepare drop samples and standards were followed, except that only half the recommended amounts of the reagents were used. 25 μl of each sample and 25 μl of steroid diluent were placed in each of two tubes for duplicate analysis. To generate a standard curve of corticosterone concentration, 25 μl of the provided standards diluted with 25 μl of DPBS, were prepared in duplicate. Standard and sample tubes were analyzed in a HP Cobra II gamma counter (Canberra-Packard, Meriden, Conn.). Corticosterone concentrations in the drop blood samples were quantified in units of ng corticosterone per punch.

Results

Figure 11:
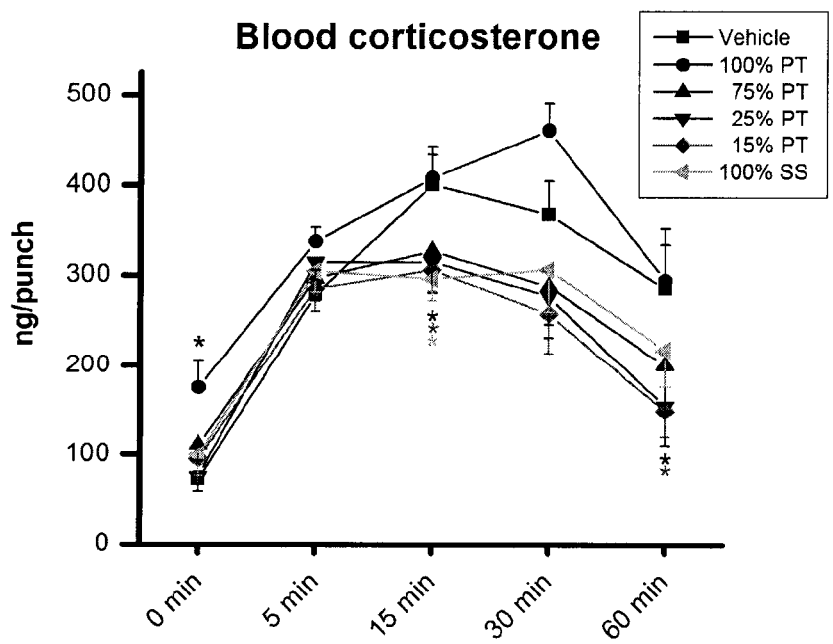
FIG. 11 shows the absolute corticosterone values obtained from venepuncture blood samples collected from all rats at baseline and 5, 10, 15, 30 and 60 min after acute mild restraint (n=48) following consecutive 3 day oral administrations of their respective treatments. * $p<0.05$ indicate significant differences from vehicle.
Figure 12:
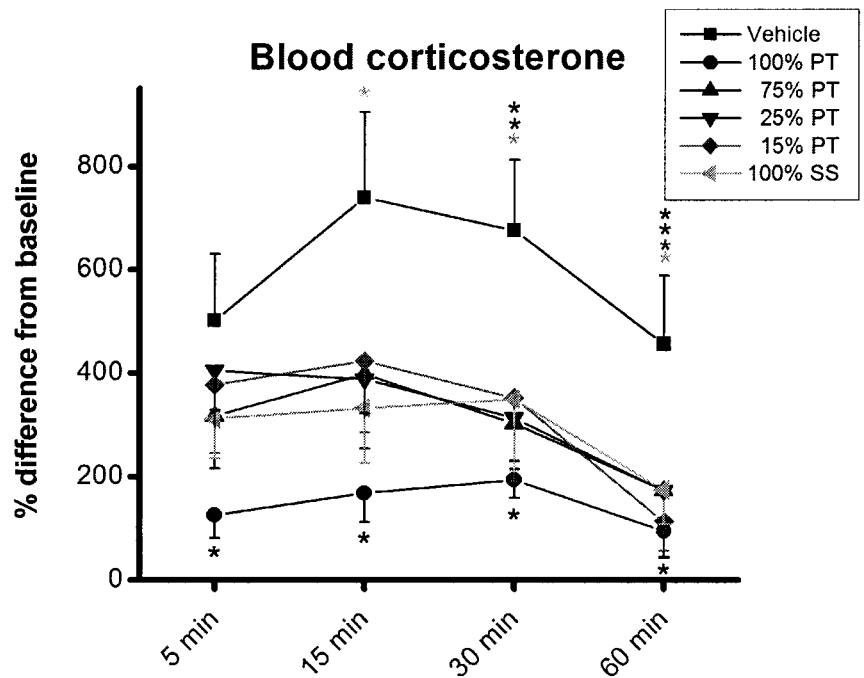
FIG. 12 shows the relative corticosterone values obtained from venepuncture blood samples collected from all rats at baseline and 5, 10, 15, 30 and 60 min after acute mild restraint (n=48) following consecutive 3 day oral administrations of their respective treatments (* $p<0.05$ indicate significant differences from vehicle).

A rise in corticosterone in the blood was observed in the untreated control rats (Group A) due to the restraint procedure that was carried out in the vehicle treated rats (FIG. 11). The treatment of the rats with the combination of plant material in the ratio of SS 75% to PT 25% ($SSPT_{7525}$), SS and PT in a ratio of SS 85% to PT 15% ($SSPT_{8515}$) and 100% SS showed a significant reduction in the stress-induced corticosterone response at the 30 min time point with unadjusted data. The 100% PT group showed a significant difference in baseline corticosterone levels from other groups. For this reason the data were adjusted to baseline (FIG. 12). In the baseline adjusted data, the % difference of corticosterone at the 30 and 60 min time points was significantly lowered.

At 60 min all treatment groups showed a lowering of cortisol. The results show that the combinations of the plant material from SS & PT were effective in lowering corticosterone in rats, compared to an untreated placebo. Further, the results also showed that all ratio of SS & PT tested were effective in treating elevated levels of stress induced corticosterone. This example demonstrates that lowering of the cortisol results in decrease of stress observed in the rats. Overall, these results and the earlier ones, in other species, support that stress with concomitant increase in glucocorticoids levels, can be reduced in animals by treating with combination of SS & PT in combination as well as individually. These results also indicate that an increase in glucocorticoids, due to other factors than stress, may be treated using the different combinations of these plants.

Example 8: Treatment of PTSD

Effect of the raw SS or PT and/or a blend (SSPT) and extracts of the same on behavioral paradigms of Fear potentiated startle (FPS) and Conditioned emotional response (CER) rodent models for PTSD.

The following example demonstrates that combination of the plant material and extracts from *Souroubea* species and *Platanus* species, are effective in decreasing freezing time in rats, in the contextual conditioned emotional response (CER) and Fear Potentiated Startle (FPS) tests.

The objective of this study was to assess the total freezing time in rats after treatment with of the two species, SS and PT and the combination, SSPT.

Materials and Methods

Raw material of SS & PT, ethanol, ethyl acetate and super critical extracts of SS & PT and combination, were prepared as follows:

(1) Raw Material: The source and preparation of *Souroubea* spp. plant vine samples (SS) and the *Platanus occidentalis* tree bark (PT) used in this experiment are described in Example 1. Samples were dried overnight in a commercial plant drier at 35° C. and ground to 2 mm mesh.

(2) Ethanol extract (EtOH): Plant material was subsequently macerated with EtOH (10 mL/g) in a food blender and the resulting dark mixture was filtered under suction in a Buchner funnel through Whatmann no 1 paper, the solids were washed with additional ethanol (5 mL/g); the alcohol and water were then evaporated, using a rotary evaporator and then under vacuum (1 mm Hg) to yield the *Souroubea* spp. crude extract (8%). The EtOH extract was partitioned between the ethyl acetate soluble fraction (EtOAc) and water-soluble fraction (f2) to provide polar and non-polar fractions (Puniani, E. 2001).

(3) EtOAc extract: The crude ethanol extracts were obtained by treating the leaves as described above. The EtOh was further extracted twice by stirring overnight with ethyl acetate. The ethyl acetate fraction (EtOAc) was evaporated to yield a gummy extract.

(4) Supercritical extracts: as described in Mullally thesis were obtained by using a SFT 250 extractor with a 100 mL vessel (Supercritical Fluid Tech., Newark, De). Samples (20 g) were extracted at 60 MPa (600 bar) nd 80 C, flow rate of 3 L/ml until a 450 g volume of $CO_2$ was consumed (25:1 solvent to biomass ration). The process provided a dark green gummy extract.

Animals: The behavioral experiments were conducted with male Sprague-Dawley rats (225-250 g body mass; Charles River Laboratories Inc., St. Constant, Quebec). Rats were housed individually and maintained under standard animal room conditions (clear Plexiglas cages, 24×30×18 cm, 12 h light-dark cycle, 21±1° C., 60% humidity, Purina Lab Chow and tap water ad libitum). All experimental procedures were approved by the Research Ethics Committee of the University of Ottawa and met the guidelines set out by the Canadian Council on Animal Care (CCAC). All attempts were made to minimize the number of animals used in the study, while maintaining the integrity of the experiments and results.

Drug Administration: The raw material plant extracts were suspended in 50% sweetened, condensed milk prior to testing and stored at 4° C. (for up to 4 days). To facilitate the mixing of the crude extract and the different fractions, all were frozen at −80° C., pulverized in an ice-cold mortar and pestle, and mixed with the 50% sweetened condensed milk.

Prior to administration of the plant materials, the rats were habituated to the treatment procedure and the taste of the drug vehicle (Eagle Brand® sweetened condensed milk diluted 50:50 with water) once a day for 5 consecutive days prior to the drug administration. Initially, all animals were gently wrapped in a blanket while the syringe containing the milk was inserted in to their cheek pocket. Since the taste of the milk was appealing, by the third administration, most of the animals freely consumed the milk from a syringe inserted between the bars of their cage. All rats were orally administered the respective treatments three times before testing—one dose on each of the 2 days preceding the test and then the $3^{rd}$ dose was administered on the test day, 1 hr prior to testing.

Behavioral Paradigms

Fear potentiated startle (FPS): The startle apparatus (Coulbourn Instruments, Whitehall, Pa., USA) consisted of a sound attenuated chamber containing two calibrated platforms (18×10 cm) designed to measure the animal's startle response. Animals were placed in a Teflon test cage (18.5×11 cm) positioned atop the platforms. The test cage floor consisted of stainless steel rods (4 mm diameter spaced 1.8 cm apart) connected to shock generators (Coulbourn Instruments; H13-16). Force changes produced by the rats' startle response were measured by the startle sensor platform. The resultant voltage output (from the platform transducer) was digitized by a computerized analog-to-digital converter, and recorded using data acquisition software (Coulbourn AASS v3.02). Startle amplitude was defined as the maximum peak-to-peak voltage that occurred during the first 200 ms after onset of the auditory startle stimulus. A high-frequency speaker, mounted (24 cm) above the platforms, generated white noise, while tones (startle stimulus) were generated by a Sonalert model tone generator (75 kHz; Coulbourn Instruments).

The training and testing for FPS spanned 4 days as has been previously described (Bédard et al., 2007). On day 1, rats were placed inside the startle chamber and exposed to random bursts of white noise (95, 110, and 115 db) for acclimatization and establishment of individual baseline startle amplitudes. On day 2, animals received a conditioning session where a tone (conditioning stimulus; CS) was paired with a shock (unconditioned stimulus; US). Specifically, a 1.0-mA, 0.5 s foot shock (US) was administered during the last 500 ms of the CS (a 4 s tone; 75 KHz). There were seven CS-US trials with an average of 1 min (randomized) inter-trial intervals (ITI). 48 h later (day 4), rats received their respective treatment 60 min before testing for fear potentiation. 20 trials of 110 db white noise bursts (random 1 min ITI) were followed by 5 trials of tones paired with noise bursts, and finally, 5 noise-alone trials. Cages were cleaned with 70% ethanol between testing of each animal. Rats that have learned to associate the CS (tone) with the US (foot shock) typically display a greater startle amplitude in the presence of the CS (Davis et al., 1993). Administration of anxiolytic compounds decrease the FPS response in rodents[7].

Conditioned emotional response (CER) test: The conditioning chamber (Coulbourn Instruments) for assessment of CER measured 31 cm×25 cm×30 cm. The front and back walls were made of clear Plexiglas and the sidewalls were made of stainless steel panels. The floor was composed of 16 stainless steel rods (4 mm diameter, 1.4 cm apart), which were connected to a shock generator (Coulbourn Instruments, model H13-16) that delivered constant current.

All subjects completed one day of training followed by a day of testing 24 hours later as has been previously described (Mountney et al., 2008; Mountney et al., 2006; Merali et al., 2008). During the contextual training phase, subjects were placed in the conditioning chamber where they received 6 foot shocks (1.0 mA; 1 second in duration) with an average inter-trial interval (ITI) of 1 min. Cued fear training comprised the delivery of 6 pairings of a 20-s tone with a 1.0 mA (1-s) continuous footshock. The shock was delivered during the final second of the 20-s tone. Again, each trial was delivered at an average ITI of 1-min. On test days, contextual fear was assessed over a 15-minute or a 20 min period by placing them in the conditioning chamber where they had previously been shocked. Freezing behavior, as defined by the absence of movement excluding involuntary respiratory activity, was assessed. Evaluations were conducted by trained experimenters blind to the treatment group. To assess the CER (in the cued condition), rats were transferred to a novel environment of similar dimensions, but visually and textually distinct from the training chamber. Specifically, black laminate covered the walls, and the floor was smooth (instead of rod-grid floor) and covered with bedding chips. Animals were allowed a 1-min exploration period and were then presented with the conditioned cue (the tone that had previously been paired with footshock). A total of 15 tones (each 20-s in duration) were presented at 1-min intervals (20 s tone+40 s ITI). Freezing was scored as described in the contextual test. Between each training and testing session, cages were cleaned with 70% ethanol.

The botanical plant materials tested were (1) 1000 mg/kg of SS, (2) 100 mg/kg PT, (3) 200 mg/kg SS:PT (in a ratio of SS 55% to PT 45% ($SSPT_{5545}$)) and (4) Control vehicle (50% sweetened condensed milk). The rats were administered orally for 3 days with their respective treatments and then tested in the contextual conditioned emotional response (CER) on total freezing time. [FIGS. 3 and 4].

Figure 13:
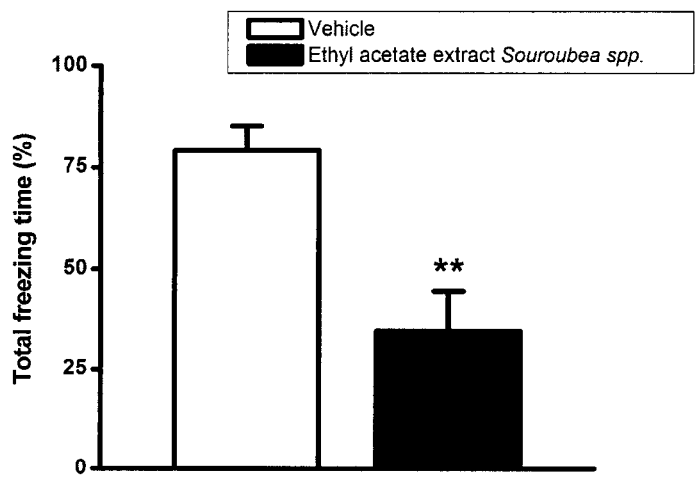
FIGS. 13 A and B shows the effects of the ethyl acetate leaf (EtOAc) extract of SS (*Souroubea* spp.) on total freezing time (%) in rats (A) in the contextual conditioned emotional response test following 3 day oral administration of 75 mg/kg. A breakdown of the group (%) freezing time is shown in (B) by time blocks * $P<0.05$, ** $P<0.005$ indicate significant differences from vehicle.
Figure 13:
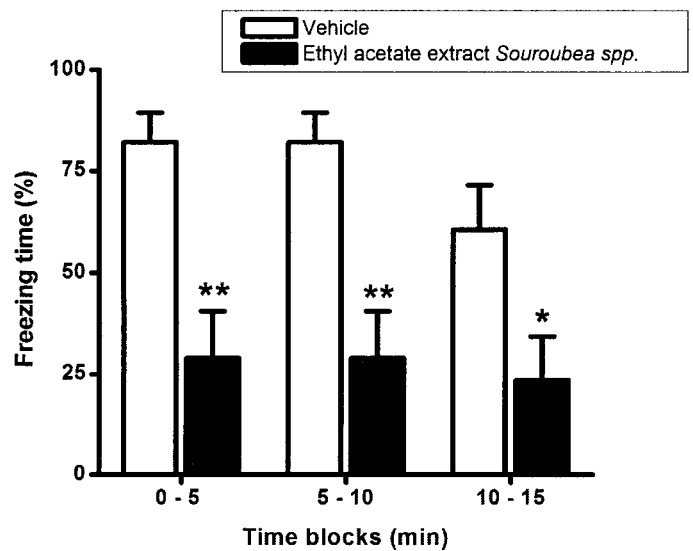

The effects of the ethyl acetate (EtOAc) leaf extract of *Souroubea* spp. on total freezing time (%) in rats (A) was examined in the contextual conditioned emotional response test after 3 day oral administration of 75 mg/kg. [FIGS. 13 A & B].

Figure 14:
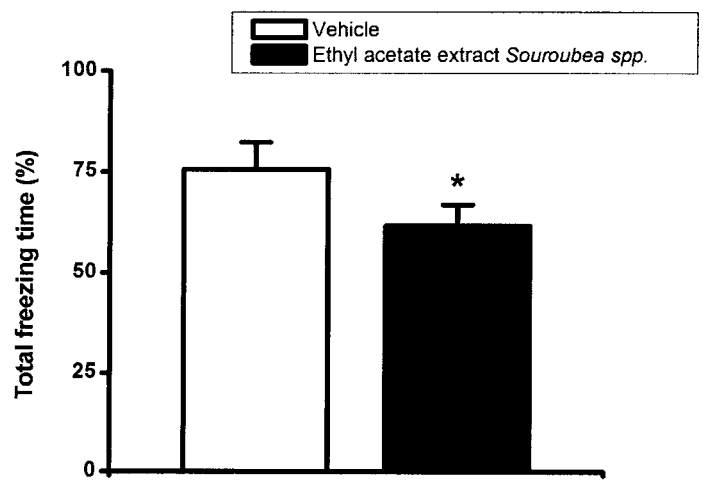
FIGS. 14 A & B show the effects of the ethyl acetate leaf (EtOAc) extract of SS on total freezing time (%) in rats (A) in the cued conditioned emotional response test following 3 day oral administration of 75 mg/kg. A breakdown of the group (%) freezing time is shown in (B) by time blocks * $P<0.05$, ** $P<0.005$ indicate significant differences from vehicle.
Figure 14:
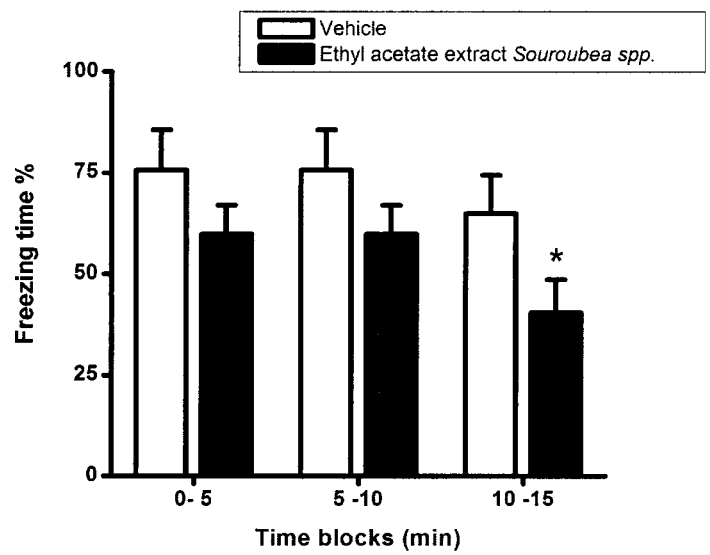

The effects of the EtOAc leaf extract of *Souroubea* spp. on total freezing time (%) in rats (A) was examined in the cued conditioned emotional response test after 3 day oral administration of 75 mg/kg. [FIGS. 14 A & B].

Figure 15:
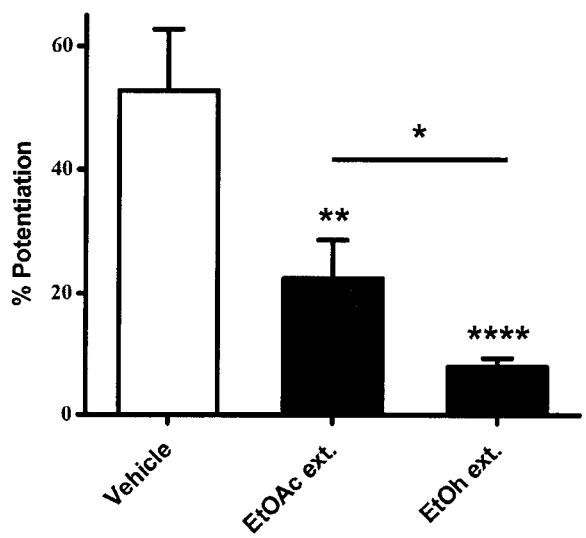
FIG. 15 shows the effects of ethanol (EtOh) and ethyl acetate (EtOAc) leaf extracts of SS on the fear potentiated startle response (FPS) in rats following 3 consecutive daily oral administrations of 100 mg/kg of their respective treatments.  $P<0.01$, ** $P<0.0001$ indicate significant differences from vehicle. * P<0.05 indicates a significant difference between ethanol (EtOh) and ethyl acetate (EtOAc) extracts.

The effect of ethanol (EtOh) and EtOAc leaf extracts of *Souroubea* spp. on the fear potentiated startle response (FPS) in rats was examined following 3 consecutive daily oral administrations of 100 mg/kg of their respective treatments. [FIG. 15]

Figure 16:
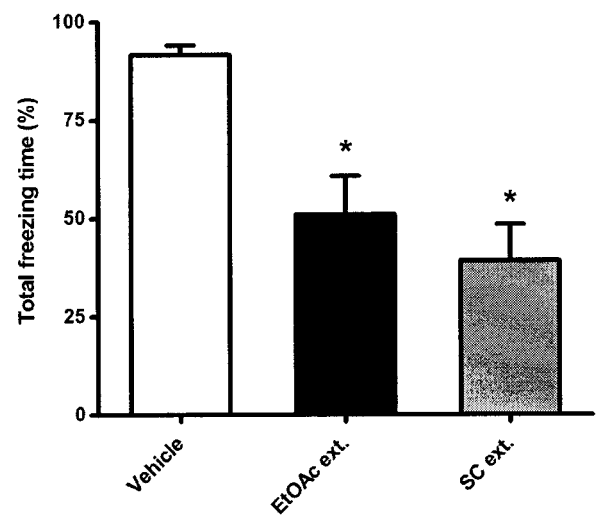
FIG. 16 shows the effects of ethyl acetate (EtOAC) and super critical (SC) leaf extracts of SS on total freezing time (%) in the first 5 min time block in rats in the contextual conditioned emotional response test following 3 day oral administration of 75 mg/kg of their respective treatments. * P<0.05 indicates significant a difference from vehicle.

The effects of EtOAc and super critical leaf extracts of SS were tested on total freezing time (%) in the first 5 min time block in rats in the contextual conditioned emotional response test following 3 day oral administration of 75 mg/kg of their respective treatments. [FIG. 16]

The effects of the orally administered EtOAc leaf extract of *Souroubea* spp. (75 mg/kg), the $GABA_A$ receptor antagonist flumazenil via i.p. injection (0.5 mg/kg) and a combination of both (EtOAc+Flu.) were tested on total freezing time in the first 5 min in the contextual CER test in rats. Oral treatments were done 60 min prior to testing and i.p. injections were given 45 min prior to testing. [FIG. 17]

Results

The botanical plant materials tested in the contextual conditioned emotional response (CER) on total freezing time, showed that the SS and the $SSPT_{5545}$ treated rats had significantly lower total freezing time compared to the rats that had been treated with the vehicle. (FIGS. 3 and 4].

Rats treated with the 3 day oral administration of 75 mg/kg of EtOAc SS leaf extract were shown to have a decrease in total freezing time, in the contextual conditioned emotional response test, when compared to the vehicle treated rats. [FIGS. 13 A & B].

Rats treated with the 3 day oral administration of 75 mg/kg of EtOAc SS leaf extract were shown to have a decrease in total freezing time, in the cued conditioned emotional response test, when compared to the vehicle treated rats. [FIGS. 14 A & B]

Rats that received 3 consecutive daily oral administrations of 100 mg/kg of the EtOh or the EtOAc leaf extracts of *Souroubea* spp. showed reduction in the fear potentiated startle response (FPS) test. [FIG. 15]

Rats that were administered EtOAc and super critical leaf extracts of SS and were tested for the total freezing time (%) in the first 5 min time block in rats in the contextual conditioned emotional response test, following 3 day oral administration of 75 mg/kg of their respective treatments. [FIG. 16]

Figure 17:
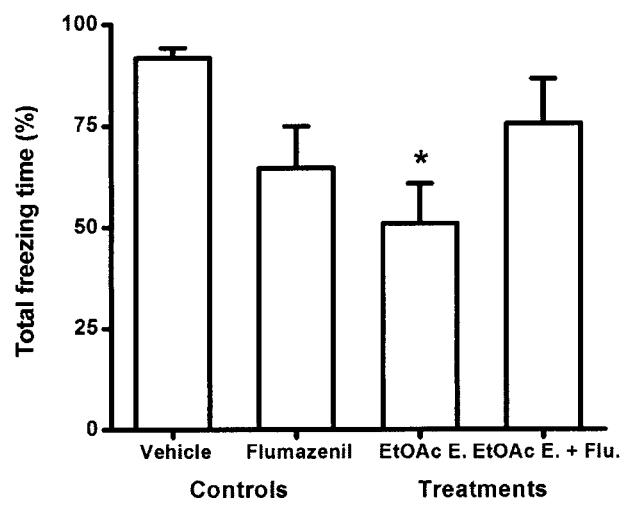
FIG. 17 shows the effects of the orally administered EtOAc leaf extract of SS (75 mg/kg), the $GABA_A$ receptor antagonist flumazenil via i.p. injection (0.5 mg/kg) and a combination of both (EtOAc extract+Flu.) on total freezing time in the first 5 min in the contextual CER test in rats

Orally administered EtOAc leaf extract (75 mg/kg) in rats showed lower total freezing time in the first 5 min in the contextual CER test compared to rats that received the $GABA_A$ receptor antagonist flumazenil (Flu.) via i.p. injection (0.5 mg/kg) or the combination of both (EtOAc+Flu.). [FIG. 17]

Discussion

All the studies on retrieval (expression) with different raw plant material and extracts have shown that when administered to rats, there is a reduction in the conditioned fear response (as measured using FPS or CER). The attenuation of the learned fear response indicates that these plants are effective at alleviating PTSD symptoms.

Many brain regions and nuclei are involved in the processes of anxiety; however there is one particular nucleus that stands out: the amygdala. The amygdaloidal complex is located within the limbic system of the central nervous system. More specifically within the cortico-temporal area of the brain and is compartmentalised into several distinct nuclei including the basolateral, medial, and central nuclei (Johansen et al., 2011). The exact functions of each nucleus are not fully understood, but the amygdala has both multiple afferent and efferent connections with most other areas of the brain such as the insula the hippocampus and the anterior cingulate cortex and plays a major role in the affective evaluation of stressful events (Davis, M. 1990).

Patients with PTSD display abnormal baseline fMRI readings in amygdalar connections (Sripada, R. K. et al, 2012). This can explain the erratic behavioral and physiological responses of these patients in absence of any aversive stimulus.

In a laboratory environment, threat-induced defensive reactions such as fear and anxiety like response can be behaviorally measured using simple but effective tests such as the Fear Potentiated Startle (FPS) and the conditioned emotional response (CER) tests. Thus fear inhibition or extinction over a short period of time (15 to 20 minutes) is measured after a previously fear conditioned rat is exposed its previous fear-eliciting context or cue in the absence of the prior aversive event. In this case the contextual box in the CER test and the auditory tone in the FPS test.

In this study the inventors used strong aversive stimuli events (multiple 1 second foot shocks, 1 mA,) to elicit a PTSD like response in rats. Other studies have used similar parameters (Davis, M. 1990; Girardi et al., 2013).

There is strong evidence that the conditioning in the CER paradigms is highly associated with amygdalar neuronal control (Spevack et al., 1975) and that the freezing response in CER is strongly associated with amygdalar GABAergic activity (Davis et al., 2006).

In FPS, it has been shown that electrolytic lesions of the amygdala block the startle response (Hitchcock, J. M. & Davis, M. 2007). Like CER, the FPS effect is highly dependant on the amygdaloid complex (Davis, M. 1990). Since the FPS paradigm is associated with loud auditory stimulus, the inventors extrapolate that this test provides similar rodent equivalent of human PTSD (Cohen et al., 2006; Morgal et al. 1995; Smith et al. 2011).

Given the comorbid nature of most anxiety disorders, it is hard to appropriately pinpoint a specific treatment for each of them (DMS-IV). Serotonin reuptake inhibitors (SSRIs) or serotonin/norepinephrine reuptake inhibitors (SNRIs) and benzodiazepines, are typically used to treat PTSD. However, these are known to have side effects. But several reports have suggested the usage of anxiolytic plants for treating the symptoms associated with PTSD (Maddox et al., 2013; Passie et al., 2012; Sarris et al., 2013). The inventors have shown that disruption of reconsolidation ultimately weakens conditioned responding and may be of therapeutic relevance to PTSD. Fear extinction refers to the decrease in fear responses during repeated presentations of the CS without the US. This is thought to be a new form of learning where a new a new inhibitory "CS-No US" memory is formed. Pharmacological approaches that enhance fear extinction are being evaluated for treatment efficacy in PTSD. The inventors have demonstrated that raw material combination and/or extracts of Marcgraviaceae and *Platanus* species disrupt reconsolidation and decrease fear responses in animal models for human PTSD.

Example 9—Treatment of Cushing's Syndrome in Horses

An older horse was presented for a veterinary examination and exhibited with a rough coat, hair not shedding out (hirsutism), a crested neck and mild founder. The mental state of the mare was described by the owners as "severely depressed like in a migraine fog, with dull glassy eyes, and head hung low". The mare was marginalized in the herd with little energy or capacity to improve her position. A tentative diagnosis of Cushing's disease was made by the veterinarian and blood samples were taken to measure ACTH and cortisol levels.

Clinical pathology results demonstrated an extremely high ACTH level of 45.4 compared to the normal range of 2-10 pmo/L and the cortisol level of 86 that was within the normal range of 50-650 nmol/L. The veterinarian confirmed the diagnosis of Cushing's disease. In horses a high level of ACTH and low level of cortisol is indicative of problem with adrenal glands which would have become exhausted when in a cushinoid state. Other species (dogs and humans) experience severe patchy hair loss when diagnosed with Cushing's due to high cortisol and normal ACTH. In contrast the horse with an exhausted adrenal, can longer produce excess cortisol and therefore the ACTH builds up to excessive levels, and a different symptom of long hairy—non shedding coat is produced Blood samples were taken from the horse before the start of the treatment and on a defined schedule to monitor the levels of ACTH and cortisol. The horse was treated with 30 grams per day of raw, dry SSPT plant material (SS to PT ratio is 50% SS and 50% PT) in a mini muffin treat format. This provided the equivalent of 1 mg of Betulinic Acid (BA)/kg body wt. The dosage form was in a mini muffin treat each containing 5 grams of SSPT/muffin. Three muffins in the morning and 3 muffins in the evening provided the daily 1× dose for the horse of 300 kg. The schedule and results are summarized in Table I below. On the blood collection days the horse was fasted (both food and SSPT) for 12 hours before sampling.

Results: Within 50 days of the SSPT treatment, the level of ACTH had dropped to 17.9 nmol/l and stabilized at between 18 and 24 nmol/I for another 5 months, while on the product. The ACTH level did not reach the normal range during the testing period. There was one test result of 8.8 pmo/L, and this may have been due to the product administration error. The mare was fed the SSPT 2 hrs prior to blood collection, whereas the blood was supposed to have been collected after fasting.

It was observed that within three days of treatment of the horse with SSPT, the depressive state had lifted, and the normal bright eyes returned. Over the next three months the fatty deposits decreased, the crested neck disappeared, the mare shed out its coat slightly early, (late February) in a normal manner 2-3 weeks before the rest of the herd. When on the SSPT product the mare had returned to a normal state of health and appeared younger in age, fit for breeding or competitive riding.

The Cortisol levels were also monitored and they were all within normal range throughout the 9 months of administration. Cortisol level did not go to sub normal levels.

The mare was taken off the treatment SSPT muffins and in 3.5 months all the original cushnoid symptoms had begun to reappear. The administration of SSPT was resumed maintenance dosage regimen.

TABLE 2

Results for SSPT on Cushing's type syndrome horse
15 year old Welsh Pony mare (Marigold)

| Normal range Day | 50-640 nmol/L Cortisol | 2-10 pmol/L ACTH |
|---|---|---|
| −17 | 86 | 45.4 |
| −3 | 92 | 39.2 |
| 0 | 90 | |
| 1 | 121 | |
| 2 | 104 | |
| 4 | 82 | |
| 8 | 140 | |
| 16 | 103 | |
| 32 | 137 | 8.8 |
| 50 | 69 | 17.9 |
| 64 | 102 | 19.1 |
| 96 | 72 | 20.3 |
| 112 | | |
| 128 | 92 | 24.4 |
| 159 | 68 | 22.2 |
| 167 | 68 | 18.5 |
| 243 | 62 | 24.2 |
| 291 (End) | | |

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Anagnostis, P., Athyros, V. G., Tziomalos, K., Karagiannis, A., Mikhailidis, D. P., 2009. The pathogenetic role of cortisol in the metabolic syndrome: A hypothesis. Journal of Clinical Endocrinology and Metabolism. 94, 2692-2701.

American Psychiatric Association. (1994). Diagnostic and statistical manual of mental disorders, $4^{th}$ Ed. (DSM-IV). Washington, D.C.

American Psychiatric Association: Diagnostic and Statistical Manual of Mental Disorders, Fifth Edition. Arlington, Va., American Psychiatric Association, 2013 (DSM-V).

Baldwin, D. S. & Polkinghorn, C. 2005, "Evidence-based pharmacotherapy of Generalized Anxiety Disorder", Int. J. Neuropsychopharmacol., vol. 8, no. 2, pp. 293-302.

Barton, B. A., 2000. Salmonid fishes differ in their cortisol and glucose responses to handling and transport stress. North American Journal of Aquaculture. 62, 12-18.

Bédard, T., Mountney, C., Kent, P., Anisman, H. & Merali, Z. Role of gastrin-releasing peptide and neuromedin B in anxiety and fear-related behavior. Behav. Brain Res. 179, 133-140 (2007)

Brown D F, Brown D D (2003). *USMLE Step 1 Secrets: Questions You Will Be Asked on USMLE Step 1*. Philadelphia: Hanley & Belfus. p. 63. ISBN 1-56053-570-9

Brown, E., Bobadilla, L., Rush, A., 2001. Ketoconazole in bipolar patients with depressive symptoms: a case series and literature review 3, 23.

Cain, C. K., Maynard, G. D. & Kehne, J. H. Targeting memory processes with drugs to prevent or cure PTSD. Expert Opin. Investig. Drugs 21, 1323-1350 (2012).

Carlson, Neil (2010). *Psychology the Science of Behaviour* [4th Canadian ed.]. Toronto, On. Canada: Pearson Canada Inc. pp. 423

Carroll, B. J., Cassidy, F., Naftolowitz, D., Tatham, N. E., Wilson, W. H., Iranmanesh, A., Liu, P. Y., Veldhuis, J. D., 2007. Pathophysiology of hypercortisolism in depression. Acta Psychiatrica Scandinavica. 115, 90-103

Chandola, T., Brunner, E., Marmot, M., 2006. Chronic stress at work and the metabolic syndrome: Prospective study. British medical journal. 332, 521-524.

Cloos, J. M. & Ferreira, V. 2009, "Current use of benzodiazepines in anxiety disorders", Curr. Opin. Psychiatry, vol. 22, no. 1, pp. 90-95.

Cohen, H., Matar, M. A., Richter-Levin, G. & Zohar, J. The contribution of an animal model toward uncovering biological risk factors for PTSD. Ann. N. Y. Acad. Sci. 1071, 335-350 (2006).

Cook, C. S., Berry, L. M., Burton, E., 2004. Prediction of in vivo drug interactions with eplerenone in man from in vitro metabolic inhibition data. Xenobiotica. 34, Courtney, R., Stewart, P. M., Toh, M., Ndongo, M.-., Calle, R. A., Hirshberg, B., 2008. Modulation of 11β-hydroxysteroid dehydrogenase (11βHSD) activity biomarkers and pharmacokinetics of PF-00915275, a selective 11αHSD1 inhibitor. Journal of Clinical Endocrinology and Metabolism. 93, 550-556.

Cruz, A. P. M., Frei, F., Graeff, F. G., 1994. Ethopharmacological analysis of rat behavior on the elevated plus-maze. Pharmacology, Biochemistry and Behavior. 49, 171-176.

Dallman, M. F. 2009. Stress-induced obesity and the emotional nervous system. Trends in Endocrinology and metabolism. 21, 159-165.

Davidson, J. R. 2009, "First-line pharmacotherapy approaches for generalized anxiety disorder", Journal of Clinical Psychiatry, vol. 70 Suppl 2, pp. 25-31

Davis, M. Pharmacological and anatomical analysis of fear conditioning. NIDA Res. Monogr. 97, 126-162 (1990).

Davis, M., Falls, W. A., Campeau, S. & Kim, M. Fear-potentiated startle: a neural and pharmacological analysis. Behav. Brain Res. 58, 175-198 (1993).

Davis, M., Myers, K. M., Chhatwal, J. & Ressler, K. J. Pharmacological treatments that facilitate extinction of fear: relevance to psychotherapy. NeuroRx J. Am. Soc. Exp. Neurother. 3, 82-96 (2006).

DePorter, T, Landsberg, G M, Araujo, J A, Ethier, J L, Bledsoe, D L. Harmonease chewable tablets reduces noise-induced fear and anxiety in a laboratory canine thunderstorm simulation: A blinded and placebo-controlled study. Journal of Veterinary Behavior: Clinical Applications and Research, Volume 7, Issue 4, July-August 2012, Pages 225-232.

Dinan, T. 2006, "Therapeutic options: Addressing the current dilemma", *European Neuropsychopharmacology*, vol. 16 Suppl 2, p. S119-S127.

Durant, C., Christmas, D., Nutt, D., 2010. The pharmacology of anxiety. Current topics in behavioral neurosciences. 2, 303-330.

Edwards, J G (1991) Clinical anxiety and its treatment. Neuropeptides, 19 S1-10

File, S. E., Lippa A. S., Beer B., Lippa M. 2004. Animal tests of Anxiety, in: Current protocols in Nuroscience, Unit 8.3 Wiley, New York, pp. 25-44.

File, S. E., 1992. Behavioral detection of anxiolytic action, in: Elliott, J. M., Heal, D. J., Marsden, C. A. (Eds.), Experimental Approaches to Anxiety and Depression, Wiley, New York, pp. 25-44.

Gallagher, P., Malik, N., Newham, J., Young, A. H., Ferrier, I. N., Mackin, P., 2008. Antiglucocorticoid treatments for mood disorders.

Gamperl, A. K., Vijayan, M. M., Boutilier, R. G., 1994. Experimental Control of Stress Hormone Levels in Fishes—Techniques and Applications. Reviews in Fish Biology and Fisheries. 4, 215-255.

Gathercole, L. L., Stewart, P. M., 2010. Targeting the pre-receptor metabolism of cortisol as a novel therapy in obesity and diabetes. Journal of Steroid Biochemistry and Molecular Biology. 122, 21-27.

Girardi, C. E. N. et al. Contextual exploration previous to an aversive event predicts long-term emotional consequences of severe stress. Front. Behav. Neurosci. 7, 134 (2013).

Gray, J. A., & McNaughton, N. (2000). *The Neuropsychology of Anxiety: An Enquiry into the Functions of the Septohippocampal System* (2nd ed.) Oxford, UK: Oxford University Press.

Hajat, A., Diez-Roux, A., Franklin, T. G., Seeman, T., Shrager, S., Ranjit, N., Castro, C., Watson, K., Sanchez, B., Kirschbaum, C., 2010. Socioeconomic and race/ethnic differences in daily salivary cortisol profiles: The Multi-Ethnic Study of Atherosclerosis. Psychoneuroendocrinology. 35, 932-943.

Herron M E, Shofer F S, Reisner I R. Retrospective evaluation of the effects of diazepam in dogs with anxiety-related behaviour problems. J Am Vet Med Assoc. 2008 Nov. 1; 233(9):1420-4.

Hitchcock, J. M. & Davis, M. Fear-potentiated startle using an auditory conditioned stimulus: effect of lesions of the amygdala. Physiol. Behav. 39, 403-408 (1987).

Jahn, H., Schick, M., Kiefer, F., Kellner, M., Yassouridis, A., Wiedemann, K., 2004. Metyrapone as additive treatment in major depression: A double-blind and placebo-controlled trial. Archives of General Psychiatry. 61, 1235-1244.

Johansen, J. P., Cain, C. K., Ostroff, L. E. & LeDoux, J. E. Molecular mechanisms of fear learning and memory. Cell 147, 509-524 (2011).

Khan, S., Michaud, D., Moody, T. W., Anisman, H., Merali, Z., 1999. Effects of acute restraint stress on endogenous adrenomedullin levels. Neuroreport 10, 2829-2833

Kim, T.-., Kim, B.-., Kim, Y.-., Yang, D. M., Han, Y.-., Dong, S. H., Kim, H. J., Chang, Y.-., Lee, J. I., Chang, R., 2003. Liver cirrhosis developed after ketoconazole-induced acute hepatic injury. Journal of gastroenterology and hepatology. 18, 1426-1429.

Kling, M. A., Coleman, V. H., Schulkin, J., 2009. Glucocorticoid inhibition in the treatment of depression: Can we think outside the endocrine hypothalamus? Depression and anxiety. 26, 641-649.

Lader, M. 1984, "Neurotransmitters and anxiety: overview", Psychopathology, vol. 17 Suppl 3, pp. 3-7.

Lawson E A, Donoho D, Miller K K, Misra M, Meenaghan E, Lydecker J, Wexler T, Herzog D B, Klibanski A. 2009, J Clin Endocrinol Metab. 2009 December; 94(12):4710-6. Epub 2009 Oct. 16.

Leblond, V. S., Bisson, M., Hontela, A., 2001. Inhibition of cortisol secretion in dispersed head kidney cells of rainbow trout (*Oncorhynchus mykiss*) by endosulfan, an organochlorine pesticide. General and Comparative Endocrinology. 121, 48-56. XVIII Li, Y, Gilbert, T. R., Matsumoto, A. H. and Weibin, S. Effect of Aging on Fatty Streak Formation in a Diet-Induced Mouse Model of Atherosclerosis. J Vasc Res. 2008; 45(3): 205-210.

Lydiard, R. B., 2003. The role of GABA in anxiety disorders. Journal of Clinical Psychiatry. 64, 21-27.

Maddox, S. A., Watts, C. S., Doyère, V. & Schafe, G. E. A naturally-occurring histone acetyltransferase inhibitor derived from Garcinia indica impairs newly acquired and reactivated fear memories. PloS One 8, e54463 (2013).

Merali, Z., Cayer, C., Kent, P. & Anisman, H. Nesfatin-1 increases anxiety- and fear-related behaviors in the rat. Psychopharmacology (Berl.) 201, 115-123 (2008).

Milot, M. R., James, J. S., Merali, Z., Plamondon, H., 2012. A refined blood collection method for quantifying corticosterone. Lab Anim. 41, 77-83

Mommsen, T. P., Moon, T. W., 1987. The metabolic potential of hepatocytes and kidney tissue in the little skate, Raja erinacea. Journal of Experimental Zoology. 244, 1-8.

Morgan, C. A., 3rd, Grillon, C., Southwick, S. M., Davis, M. & Charney, D. S. Fear-potentiated startle in posttraumatic stress disorder. Biol. Psychiatry 38, 378-385 (1995).

Mountney, C., Anisman, H. & Merali, Z. Effects of gastrin-releasing peptide agonist and antagonist administered to the basolateral nucleus of the amygdala on conditioned fear in the rat. Psychopharmacology (Berl.) 200, 51-58 (2008).

Mountney, C., Sillberg, V., Kent, P., Anisman, H. & Merali, Z. The role of gastrin-releasing peptide on conditioned fear: differential cortical and amygdaloid responses in the rat. Psychopharmacology (Berl.) 189, 287-296 (2006)

Mullally, M., Kramp, K., Cayer, C., Saleem, A., Ahmed, F., McRae, C., Baker, J., Goulah, A., Otorola, M., Sanchez, P., Garcia, M., Poveda, L., Merali, Z., Durst, T., Trudeau, V. L., Arnason, J. T., 2011. Anxiolytic activity of a supercritical carbon dioxide extract of *Souroubea sympetala* (Marcgraviaceae). Phytother. Res. PTR 25, 264-270.

Parker, K. J., Schatzberg, A. F., Lyons, D. M., 2003. Neuroendocrine aspects of hypercortisolism in major depression. Hormones and Behavior. 43, 60-66.

Parsons, R. G. & Ressler, K. J. Implications of memory modulation for post-traumatic stress and fear disorders. Nat. Neurosci. 16, 146-153 (2013).

Passie, T., Emrich, H. M., Karst, M., Brandt, S. D. & Halpern, J. H. Mitigation of post-traumatic stress symptoms by Cannabis resin: a review of the clinical and neurobiological evidence. Drug Test. Anal. 4, 649-659 (2012).

Pellow, S., Chopin, P., File, S. E., Briley, M., 1985. Validation of open: closed arm entries in an elevated plus-maze as a measure of anxiety in the rat. Journal of Neuroscience Methods. 14, 149-167.

Ponomarev, I., Rau, V., Eger, E. I., Harris, R. A. & Fanselow, M. S. Amygdala transcriptome and cellular mechanisms underlying stress-enhanced fear learning in a rat model of posttraumatic stress disorder. Neuropsychopharmacol. Off. Publ. Am. Coll. Neuropsychopharmacol. 35, 1402-1411 (2010).

Puniani, E. Novel Natural Product Based Anti-anxiety Therapy and Natural Insecticides. Thesis (2001).

Rostagno, M. H., 2009. Can stress in farm animals increase food safety risk? Foodborne Pathogens and Disease. 6, 767-776.

Ruyet, J. P.-., Labbé, L., Bayon, N. L., Sévère, A., Roux, A. L., Delliou, H. L., Quéméner, L., 2008. Combined effects of water quality and stocking density on welfare and growth of rainbow trout (*Oncorhynchus mykiss*). Aquatic Living Resources. 21, 185-195. XXII Sarris, J., McIntyre, E. & Camfield, D. A. Plant-based medicines for anxiety disorders, part 2: a review of clinical studies with supporting preclinical evidence. CNS Drugs 27, 301-319 (2013).

Schreck, C. B., Contreras-Sanchez, W., Fitzpatrick, M. S., 2001. Effects of stress on fish reproduction, gamete quality, and progeny. Aquaculture. 197, 3-24.

Sharma, S. T., Nieman, L. K., 2011. Cushing's syndrome: All variants, detection, and treatment. Endocrinology and metabolism clinics of North America. 40, 379-391.

Sheehan, D. V. & Sheehan, K. H. 2007, "Current approaches to the pharmacologic treatment of anxiety disorders", *psychopharmacology bulletin*, vol. 40, no. 1, pp. 98-109.

Smith, K. S. et al. Reduction of fear-potentiated startle by benzodiazepines in C57BL/6J mice. Psychopharmacology (Berl.) 213, 697-706 (2011).

Smith, G. D., Ben-Shlomo, Y., Beswick, A., Yarnell, J., Lightman, S., Elwood, P., 2005. Cortisol, testosterone, and coronary heart disease: Prospective evidence from the caerphilly study. Circulation. 112, 332-340.

Somers, J. M., Goldner, E. M., Waraich, P., & Hsu, L. 2006, "Prevalence and incidence studies of anxiety disorders: a systematic review of the literature", Can. J. Psychiatry, vol. 51, no. 2, pp. 100-113.

Spevack, A. A., Campbell, C. T. & Drake, L. Effect of amygdalectomy on habituation and CER in rats. Physiol. Behay. 15, 199-207 (1975).

Sripada, R. K. et al. Altered resting-state amygdala functional connectivity in men with posttraumatic stress disorder. J. Psychiatry Neurosci. JPN 37, 241-249 (2012).

Starkman, M. N., Giordani, B., Berent, S., Schork, M. A., Schteingart, D. E., 2001. Elevated cortisol levels in Cushing's disease are associated with cognitive decrements. Psychosomatic medicine. 63, 985-993.

Steimer, T. Animal models of anxiety disorders in rats and mice: some conceptival issues. Dialogues Clin neurosci 2011, 13, 495-506.

Stewart, P. M., 2003. The adrenal cortex. in: Larsen, P. R., Kronenberg, H. M., Melmed, S., Polonsky, K. S. (Eds.), Williams textbook of endocrinology, 10th ed. Saunders, Philadelphia, pp. 491-551

Tindle, H. A., Davis, R. B., Phillips, R. S., & Eisenberg, D. M. 2005, "Trends in us of complementary and alternative medicine by US adults: 1997-2002", *Alternative Therapies in Health and Medicine*, vol. 11, no. 1, pp. 42-49.

Thomson, F., Craighead, M., 2008. Innovative Approaches for the Treatment of Depression:Targeting the HPA Axis 33, 691.

Travison, T. G., O'Donnell, A. B., Araujo, A. B., Matsumoto, A. M., McKinlay, J. B., 2007. Cortisol levels and measures of body composition in middle-aged and older men. Clinical Endocrinology. 67, 71-77.

Trenzado, C. E., Morales, A. E., de la Higuera, M., 2008. Physiological changes in rainbow trout held under crowded conditions and fed diets with different levels of vitamins E and C and highly unsaturated fatty acids (HUFA). Aquaculture. 277, 293-302.

Walker, D. L. & Davis, M. Quantifying fear potentiated startle using absolute versus proportional increase scoring methods: implications for the neurocircuitry of fear and anxiety. Psychopharmacology (Berl.) 164, 318-328 (2002).

Wolkowitz, O. M., Reus, V. I., Chan, T., Manfredi, F., Raum, W., Johnson, R., Canick, J., 1999. Antiglucocorticoid treatment of depression: Double-blind ketoconazole. 45, 1070.

Zar, J. H., 1999. Biostatistical Analysis, Fourth Edition, Prentice Hall, Upper Saddle River, N.J.

The invention claimed is:

1. A composition comprising A) a preparation obtained from a *Souroubea gilgii* plant and B) a preparation obtained from a *Platanus occidentalis* plant; wherein the ratio of A:B is from 40:60 to 60:40.

2. The composition of claim 1, wherein the ratio of A:B is 55:45.

3. The composition of claim 1, further comprising a carrier.

4. The composition of claim 1, further comprising an additional anxiolytic agent or an additional glucocorticoid decreasing agent.

* * * * *